US007195906B2

(12) United States Patent
Collins et al.

(10) Patent No.: US 7,195,906 B2
(45) Date of Patent: Mar. 27, 2007

(54) BIFIDOBACTERIUM IN THE TREATMENT OF INFLAMMATORY DISEASE

(75) Inventors: John Kevin Collins, Doughcloyne (IE); Gerald Christopher O'Sullivan, Cork (IE); Liam O'Mahony, Cork (IE); Fergus Shanahan, Kinsale (IE)

(73) Assignees: Enterprise Ireland (Trading as BioResearch Ireland), Cork (IE); University College Cork--National University of Ireland, Cork (IE)

( * ) Notice: Subject to any disclaimer, the term of this patent is extended or adjusted under 35 U.S.C. 154(b) by 0 days.

(21) Appl. No.: 10/783,020

(22) Filed: Feb. 23, 2004

(65) Prior Publication Data
US 2005/0074441 A1    Apr. 7, 2005

Related U.S. Application Data

(63) Continuation of application No. 09/903,681, filed on Jul. 13, 2000, now abandoned, which is a continuation of application No. PCT/IE00/00008, filed on Jan. 17, 2000.

(30) Foreign Application Priority Data

Jan. 15, 1999   (IE)   .................................   1999/0033
Sep. 20, 1999   (IE)   .................................   1999/0782

(51) Int. Cl.
*C12N 1/20*         (2006.01)
*A01N 63/00*        (2006.01)

(52) U.S. Cl. ............... 435/252.1; 435/252.9; 435/252.4; 435/822; 435/853; 424/93.4; 424/93.45; 424/93.3

(58) Field of Classification Search ............ 435/252.9, 435/252.1, 252.4, 822, 853; 424/93.4, 93.45, 424/933
See application file for complete search history.

(56) References Cited

U.S. PATENT DOCUMENTS

| 4,347,240 | A |   | 8/1982  | Mutai et al. |
|-----------|---|---|---------|--------------|
| 4,435,389 | A |   | 3/1984  | Mutai et al. |
| 5,032,399 | A |   | 7/1991  | Gorbach et al. |
| 5,443,826 | A |   | 8/1995  | Borody |
| 5,711,977 | A |   | 1/1998  | Yang et al. |
| 5,834,423 | A | * | 11/1998 | Koketsu et al. .............. 514/7 |
| 5,922,375 | A |   | 7/1999  | Luchansky et al. |
| 6,025,008 | A | * | 2/2000  | Akahoshi et al. ........... 426/583 |
| 6,077,504 | A | * | 6/2000  | Cavaliere ved. Vesley et al. ........................ 424/93.3 |
| 6,132,710 | A |   | 10/2000 | Panigraphi et al. |
| 6,368,591 | B1| * | 4/2002  | Chen et al. .............. 424/93.45 |
| 6,645,530 | B1|   | 11/2003 | Borody |
| 2002/0006432 | A1 |  | 1/2002  | Collins et al. |
| 2003/0170217 | A1 |  | 9/2003  | Collins et al. |
| 2003/0215467 | A1 |  | 11/2003 | Collins et al. |
| 2005/0214272 | A1 |  | 9/2005  | Collins et al. |
| 2006/0002908 | A1 |  | 1/2006  | Collins et al. |

FOREIGN PATENT DOCUMENTS

| EP | 0 508 701 B1 | 7/1996 |
|----|--------------|--------|
| EP | 0 904 784 A1 | 3/1999 |
| EP | 0 384 319 B1 | 4/1999 |
| EP | 1 312 667 A1 | 5/2003 |
| GB | 1 503 094    | 3/1978 |
| JP | 9241173      | 9/1997 |
| RU | 2 091 075 C1 | 9/1997 |
| RU | 2 109 054 C1 | 4/1998 |
| WO | WO 89/05849 A1 | 6/1989 |
| WO | WO 90/01335 A1 | 2/1990 |
| WO | WO 90/09398 A1 | 8/1990 |
| WO | WO 97/35596 A1 | 10/1997 |
| WO | WO 98/00035 A1 | 1/1998 |
| WO | WO 98/35014   * | 8/1998 |
| WO | WO 98/35014 A2 | 8/1998 |
| WO | WO 99/51631 A1 | 10/1999 |
| WO | WO 99/62348 A1 | 12/1999 |
| WO | WO 01/37865 A1 | 5/2001 |

OTHER PUBLICATIONS

Kim et al. Korean Journal of Dairy Science, (1998) vol. 20, Mo. 3, pp. 191-204.*
Yildirim et al., "Characterization and antimicrobial spectrum of bifidocin B, a bacteriocin produced by Bifidobacterium bifidum NCFB 1454," J Food Prot, 61(1):47-51, (1998), Abstract Only.
Adachi, Susumu, "Lactic Acid Bacteria and the Control of Tumours," The Lactic Acid Bacteria, 1:233-261, (1992).
Anand et al., "Antibacterial Activity Associated with Bifidobacterium bifidum—II," Cult. Dairy Prod, pp. 21-23, (1985). (Attached copy is missing 1 page).
Arai et al., "Cytokines: Coordinators of Immune and Inflammatory Responses," Annual Rev. Biochem., 59:783-836, (1990).
Aranda et al., "Analysis of Intestinal Lymphocytes in Mouse Colitis Mediated by Transfer of CD4+, CD45RB$^{high}$ T Cells to SCID Recipients[1]," Jour. of Immunology, 158(7):3464-3473, (1997).
Arihara, et al., "Salivacin 140, a novel bacteriocin from *Lactobacillus salivarius* subsp. salicinius T140 active against pathogenic bacteria," Letters in Applied Microbiology, 22:420-424, (1996).
Bachwich, et al., "Tumor Necrosis Factor Stimulates Interleukin-1 and Prostaglandin $E_2$ Production in Resting Macrophages," Biochemical and Biophysical Res. Comm., 136(1):94-101, (1986).
Blum et al., "Adhesion studies for probiotics: need for validation and refinement," Trends in Food Science & Technology, 10:405-410 (1999).

(Continued)

*Primary Examiner*—Vera Afremova
(74) *Attorney, Agent, or Firm*—Wolf, Greenfield, & Sacks, P.C.

(57) ABSTRACT

A strain of *Bifidobacterium* isolated from resected and washed human gastrointestinal tract is significantly immunomodulatory following oral consumption in humans. The strain is useful in the prophylaxis and/or treatment of undesirable inflammatroy activity, especially gastrointestinal inflammatory activity such as inflammatory bowel disease or irritable bowel syndrome. The inflammatory activity may also be due to cancer.

33 Claims, 13 Drawing Sheets

OTHER PUBLICATIONS

Bouhnik et al., "Effects of Bifidobacterium sp fermented milk ingested with or without inulin on colonic bifidobacteria and enzymatic activities in healthy humans," Eur. Jour. Clin. Nut., 50:269-273, (1996).

Bouhnik et al., "Survie et effets chez l'homme des bactéries ingérées dans less laits fermentés," LAIT, 73:241-247, (1993).

Brandtzaeg et al., "Immunopathology of human inflammatory bowel disease," Springer Semin Immunopath, 18:555-589, (1997).

Brink et al., "Antimicrobial activity of lactobacilli: preliminary characteristization and optimization of production of acidocin B a novel bacteriocin produced by *Lactobacillus acidophilus* M," Jour. of Applied Bacteriology, 77:140-148, (1994).

Brzuszczak et al., "Cyclic AMP-dependent anion secretion in human small and large intestine," Jour. of Gastroenterology and Hepatology, 11:804-810, (1996).

Charteris et al., "Antibiotic susceptibility of potentially probiotic Bifidobacterium isolates from the human gastrointestinal tract," Letters in Applied Microbiology, 26:333-337, (1998).

Charteris et al., "Selective detection, enumeration and identification of potentially probiotic Lactobacillus and Bifidobacterium species in mixed bacterial populations," Int. Jour. of Food Microbiology, 35:1-27, (1997).

Charteris, et al., "Antibiotic Susceptibility of Potentially Probiotic Lactobacillus Species," Jour. Food Protection, 61(12):1636-1643, (1998).

Charteris, et al., "Development and application of an in vitro methodology to determine the transit tolerance of potentially probiotic Lactobacillus and Bifidobacterium species in the upper human gastrointestinal tract," Jour. of Applied Microbiology, 84:759-768, (1998).

Chauvière et al., "Adhesion of human *Lactobacillus acidophilus* strain LB to human eterocyte-like Caco-2 cells," Journal of General Microbiology, 138:1689-1696, (1992).

Chevalier et al., "Detection of Bifidobacterium species by enzymatic methods," Jour. of Appl. Bacteriology, 68:619-624, (1990).

Cicco et al., "Inducible Production of Interleukin-6 by Human Polymorphonuclear Neutrophils: Role of Granulocyte-Macrophage Colony-Stimulating Factor and Tumor Necrosis Factor-alpha," Blood, 75(10):2049-2052, (1990).

Collins et al., "A Controlled Trial of Probiotic Treatment of IL-10 Knockout Mice," Gastroenterology, 116(4):1 page, (1999). Abstract G2981.

Collins et al., "Demonstration of Probiotic Function in a Double Blind Placebo Controlled Clinical Trials in Adults," Functional Food Research in Europe, pp. 40-41, (1998).

Collins et al., "Probiotics and Man—The Host Microbe Interface," Gastroenterology, 116(4):1 page, (1999). Abstract G2982.

Collins et al., "Selection of Probiotic Strains for Human Applications," Int. Dairy Journal, 8:487-490, (1998).

Collins, "Probiotic Lactobacilli-Towards Defining Selection and Functional Criteria," Demonstration Fair CT96-1028, p. 27, (1996).

Collins, "Selection of Probiotic Strains and Potential Therapeutic Applications," Book of Abstracts from Eur. Comm. Biotech and Fair Prog., p. L-2, (1995).

Collins et al., "Probiotic bacteria-interaction with the human immune system," Int. Congress and Symp. Series 219, pp. 13-17, (1996).

Collins, J.K., "Probiotics and Inflammatory Bowel Disease: Animal Models," Functional Food Research in Europe, p. 124, (1998).

Cong et al., "Genes, Bacteria, and T Cells: Ingredients for Inflammatory Bowel Disease," Gastroenterology, 115:1595-1596, (1998). (Summary by Shanahan, O'Sullivan, and Collins).

Crabbe et al., "The Normal Microbial Flora as a Major Stimulus for Proliferation of Plasma Cells Synthesizing IgA in the Gut," Int. Arch. Allergy 34:362-375, (1968).

Daly et al., "Biotechnology of lactic acid bacteria with special reference to bacteriophage resistance," Antonie Van Leewenhoek, 70:99-110, (1996).

Darveau, Richard, "Infection, inflammation, and cancer," Nature Biotechnology, 17:19, (1999).

Dawson et al., "18 pH, buffers, and physiological media," Data For Biochemical Research, pp. 417-448, (1969).

Dekker et al., "Sensitive Pulsed Amperometric Detection of Free and Conjugated Bile Acids in Combination with Gradient Reversed-Phase HPLC," Chromatographia, 31(11/12):549-553, (1991).

Dinarello et al., "New Concepts on the Pathogenesis of Fever," Reviews of Infectious Diseases, 10(1):168-189, (1988).

Donnelly, et al., "Differential Regulation of IL-1 Production in Human Monocytes by IFN-γ and IL-4," Journal of Immunology, 145(2):569-575, (1990).

Dunne et al., "Epithelial Adhesion of Probiotic Microorganisms in vitro and in vivo," Gastroenterology, 116(4):1 page, (1999). Abstract G3058.

Dunne et al., "Probiotics: from myth to reality. Demonstration of functionality in animal models of disease and in human clinical trials," Antonie Van Leeuwenhoek, XP000929178, 76:279-292, (1999) (Jul.-Nov., 1999).

Favier et al., "Fecal β-D-Galactosidase Production and Bifidobacteria Are Decreased in Crohn's Disease," Digestive Diseases and Sci., 42(4):817-822, (1997).

Feency et al., "Lack of Specific Systemic Immune Response on Oral Consumption of Probiotic Lactobacilli," Int. Dairy Journal, 8(5/6):1 page, (1998).

Ferrante et al., "Effects of Tumour Necrosis Factor Alpha and Interleukin-1 Alpha and Beta on Human Neutrophil Migration, Respiratory Burst and Degranulation," Int. Archs Allergy Appl. Immun., 86:82-91, (1988).

Flynn et al., "Isolation and Characterisation of the Novel Anitbacterial Proteins, ABP-1 and ABP-118 from Human Isolates *Lactobacillus salivarius* subsp. salivarius UCC-1 and UCC-118," Intl. Dairy Jour., 8(5/6):1 page, (1998).

Fuller, "Probiotics in man and animals," Jour. of Applied Bacteriology, 66:365-378, (1989).

Gahan et al., "Innate resistance to Listeria monocytogenes in tumor-bearing mice," Jour. of Leukocyte Biology, 62:726-732, (1997).

Ganguly et al., "Mechanism of action of cholera toxin & other toxins," Indian J. Med. Res., 104:28-37, (1996).

Gardiner et al., "Characterisation of Cheddar Cheese Harboring Probiotic Lactobacillus Adjuncts," Int. Dairy Journal, 8(5/6):597, (1998).

Gardiner et al., "Cheddar Cheese as a Probiotic Delivery System," Sixth Symposium on Lactic Acid Bacteria, Abstract J28, (1999).

Gardiner et al., "Evaluation of Cheddar Cheese as a Food Carrier for Delivery of a Probiotic Strain to the Gastrointestinal Tract," J. Dairy Sci., 82:1379-1387, (1999).

Gardiner et al., "Influence of a Probiotic Adjunct Culture of *Enterococcus faecium* on the Quality of Cheddar Cheese," J. Argic. Food Chem., 47:4907-4916, (1999).

Gardiner et al., "Preparation of Spray Dried Powders Harbouring High Levels of Probiotic Lactobacilli," Sixth Symp. on Lactic Acid Bacteria, Abstract J29, (1999).

Gardiner, et al., "Development of a Probiotic Cheddar Cheese Containing Human-Derived *Lactobacillus paracasei* Strains," Applied and Env. Microbiology, pp. 2192-2199, (1998).

Gatanaga et al., "Purification and characterization of an inhibitor (soluble tumor necrosis factor receptor) for tumor necrosis factor and lymphotoxin obtained from the serum ultrafiltrates of human cancer patients," Proc. Natl. Acad. Sci, 87:8781-8784, (1990).

Gibson, Glenn, "Dietary modulation of the human gut microflora using prebiotics," Jour. of Nutrition, 80(2):S209-S212, (1998).

Gilliland, Stanley, "Health and nutritional benefits from lactic acid bacteria," FEMS Microbiology Reviews, 87:175-188, (1990).

Gionchetti et al., "Microflora in the IBD Pathogenesis: Possible Therapeutic Use of Probiotics" Gastroenterology Intl., 11(1):108-110, (1998).

Groot, J.A., "Correlation between electrophysiological phenomena and transport of macromole-cules in intestinal epithelium," The Veterinary Quarterly, 20(3):S45-S49, (1998).

Halpern et al., "Treatment of Irritable Bowel Syndrome with Lacteol Fort: A Randomized, Double-Blind, Cross-Over Trial," Am Jour. of Gastroenterology, 91(8):1579-1585, (1996).

Henderson et al., "Cytokines, homeostasis, networks and disease," Bacteria-Cytokine Interactions in Health and Disease, pp. 79-130, (1998).

Houde et al., "Treatment of Acute Enteritis with Oral Administration of Short-Term High-Dose Bifidobacteria," Chinese Jour of Microecology, 6(6):47, (1994).

Huis et al., "Establishing a scientific basis for probiotic R&D," 12:6-8, (1994).

Inagaki et al., "Causes of Death in Cancer Patients," Cancer, 33(2):568-573, (1974).

Isolauri et al., "Oral Bacteriotherapy for Viral Gastroenteritis," Digestive Diseases and Sciences, 39(12):2595-2600, (1994).

Jinggang, Lan, "Immunopotentiating Activity of Bifidobacterium and Its Significance," For. Med. Sci., Clinic Biochem & Med Test, 19(5):231-233, (1998).

Jong, S.C., "Probiotics for Humans and Animals," ATCC Quarterly Newsletter, 13(1):1-4, (1993).

Kagnoff, "Immunology of the Intestinal Tract," Gastroenterology, 105:1275-1280, (1993).

Kato et al., "Suppressive Effects of the Oral Administration of Lactobacillus Casei on Type II Collagen-Induced Arthritis in DBA/1 Mice," Life Sciences, 63(8):635-644, (1998).

Kawakami et al., "A Group of Bactericidal Factors Conserved by Vertebrates For More Than 300 Million Years," Journal of Immunology, 132(5):2578-2581, (1984).

Kim et al., "The Properties of Bifidobacteria Isolated from Korean," Korean Journal of Dairy Science, 20(3):191-204, (1998).

Kim, Hyung, "Characterization of Lactobacilli and Bifidobacteria as applied to Dietary Adjuncts[1]," Cultured Dairy Products Journal, pp. 6-9, (1988).

Klaenhammer, Todd, "Genetics of bacteriocins produced by lactic acid bacteria," FEMS Microbiology Rev., 12:39-86, (1993).

Kühn, et al., "Interleukin-10-Deficient Mice Develop Chronic Enterocolitis," Cell, 75:263-274, (1993).

Kulkarni et al., "Inhibitory Effect of Bifidobacterium longum Cultures on the Azoxymethane-Induced Aberrant Crypt Foci Formation and Fecal Bacterial β-Glucuronidase," Proc. Soc. Experim. Biol. Med., 207:278-283, (1994).

Lamm et al., "Interaction of antigens and antibodies at mucosal surfaces," Ann Rev Microbiol, 51:311-40, (1997). (Previously cited as Ramos et al.).

Lee et al., "The coming of age of probiotics, Trends in Food Science & Technology," 6:241-245, (1995).

Legrand-Defretin et al., "Ion-Pair High-Performance Liquid Chromatography of Bile Salt Conjugates: Application to Pig Bile," LIPIDS, 26(8):578-583, (1991).

Leonard, et al., "Regulation of the Inflammatory Response in Animal Models of Multiple Sclerosis by Interleukin-12," Critical Reviews in Immunology, 17:545-553, (1997).

Lucey et al., "Developing Fields in Food Biotechnology," Food Science and Technology, 11(4):230-233, (1993).

Madsen et al., "*Lactobacillus SP* prevents development of enterocolitis in interleukin-10 gene deficient mice," Gastroenterology, 112(4):1030, (1997).

Malefyt et al., "Interleukin 10 (IL-10) and Viral IL-10 Strongly Reduce Antigen-specific Human T Cell Proliferation by Diminishing the Antigen-presenting Capacity of Monocytes via Downregulation of Class II Major Histrocompatibility Complex Expression," J. Exp. Med., 174:915-924, (1991).

Mangan et al., "Lipopolysaccharide, Tumor Necrosis Factor-α, and IL-1β Prevent Programmed Cell Death (Apoptosis) in Human Peripheral Blood Monocytes," Journal of Immunology, 146(5):1541-1546, (1991).

Marteau et al., "Potential of using lactic acid bacteria for therapy and immunomodulation in man," FEMS Microbiology Reviews, 12:207-220, (1993).

Mattila-Sandholm, "Novel Methods for Probiotic Research," Demonstration Project Fair2 CT96-1028, pp. 11-15, (1997).

Mattila-Sandholm, et al., "Probiotics: towards demonstrating efficacy," Trends in Food Sci & Tech., 10:393-399, (1999).

McBrearty et al., "Probiotic Bifidobacteria and Their Identification Using Molecular Genetic Techniques," Proc. of British Nutritional Foundation, pp. 97-107, (2000).

McCracken, et al., "Probiotics and the Immune System," Probiotics a Critical Review, pp. 85-113, (1999).

McFarland, et al., "Pharmaceutical Probiotics for the Treatment of Anaerobic and Other Infections," Anaerobe, 3:73-78 (1997).

McGee et al., "A synergistic relationship between TNF-α, IL-1β, and TGF-β1 on IL-6 secretion by the IEC-6 intestinal epithelial cell line," Immunology, 86:6-11, (1995).

Medaglini et al., "Mucosal and systemic immune responses to a recombinant protein expressed on the surface of the oral commensal bacterium *Streptococcus gordonii* after oral colonization," Proc. Natl. Acad. Sci, 92:6868-6872, (1995).

Mestan et al., "Antiviral effects of recombinant tumour necrosis factor *in vitro*." Nature. 323:816-819, (1986). (Previously cited as Wong et al.).

Morrisey et al., "Election of a Probiotic Strain to Modify Human Gut Flora and a Controlled Trial of Delivery and Efficacy," Ir. Soc. of Gastroenterology, 167(8):7, (1998).

Murphy et al., "Evaluation and Characterisation of Probiotic Therapy in the CD45RB[HI] Transfer Model of Colitis," Gastroenterology, 116(4):A780, (1999). Abstract 3382.

Murphy et al., "Long-term Colonisation with *Lactobacillus salivarius* subsp. salivarius UCC118: A Probiotic Candidate," Intl. Dairy Journal, 8(5/6):3 pages, (1998).

Murphy, et al., "In vivo assessment of potential probiotic *Lactobacillus salivarius* strains: evaluation of their establishment, persistence, and localisation in the murine gastrointestinal tract." Microbiol. Ecology in Health and Disease, pp. 149-157, (1999).

Neutra et al., "M Cells as a Pathway for Antigen Uptake and Processing," Essentials of Mucosal Immunology, 196:29-35, (1996).

O'Halloran et al., "Adhesion of Potential Bacteria to Human Epithelial Cell Lines," Intl. Dairy Jour., 8(5/6):3 pages, (1998).

Oksanen et al., "Prevention of Travellers' Diarrhoea by Lactobacillus GG," Annual Med., 22(1):53-56, (1990).

O'Mahony et al., "Probiotic Bacteria and Pathogenic Bacteria Elicit Differential Cytokine Responses From Dendritic Cells," XP001097379, (2001). Abstract 1625.

O'Mahony et al., "Probiotic Bacteria and the Human Immune System," Sixth Symp. on Lactic Acid Bacteria, pp. 63-70, (1999).

O'Mahony, et al., "Consumption of Probiotic Bacteria Ameliorates Enterocolitis in IL-10 Knock Out Mice," Irish Jour. Med. Sci, 168(5):9, (1999).

O'Mahony, et al., "UCC118 Modulates Proinflammatory Cytokine Production In Vitro," Ir. J. Med. Sci., 168(9), (1999).

O'Mahony et al., "Probiotic Treatment of Enterocolitis in IL-10 Knock Out Mice." Sixth Symp on Lactic Acid Bacteria. 2 pages. Sep. 19/23, 1999. Abstract J30.

O'Riordan, et al., "Assessment of Bifidobacterium Strains for Antimicrobial and Exopolysaccharide Production and Evaluation of Pulsed-field Gel Electrophoresis as a Method for Identifying or Discriminating between Bifidobacterial Strains," Intl. Dairy Jour., 8(5/6): 3 pages (1998).

O'Riordan et al., "Determination of genetic diversity within the genus Bifidobacterium and estimation of chromosomal size," FEMS Microbiology Letters, 156:259-264, (1997).

O'Riordan et al., "Evaluation of bifidobacteria for the production of antimicrobial compounds and assessment of performance in cottage cheese at refrigeration temperature," Journal of Applied Microbiology, 85:103-114, (1998).

O'Sullivan et al., "Isolation and Selection of Normal Gut Microflora for Use as Prophylactic Probiotic Agents," Irish Society of Gastroenterology, Proc. in Dublin, Jun. 7-8, 1991, pp. 419-420.

O'Sullivan et al., "Probiotic Bacteria in the Human Gastro Intestinal Tract (Myth or Reality)," Irish Jour of Med Sci, Proc. of the Irish Soc. of Gastroenterology, Dec. 4-5, 1992, p. 273.

O'Sullivan et al., "Probiotic bacteria: myth or reality?," Trends in Food Science & Technology, 3:309-314, (1992).

O'Sullivan et al., "The Human Gut as a Source of Probiotic Bacteria—Myth or Reality?" Irish Jour. of Med. Sci., p. 25, (1993).

Panwala, et al., "A Novel Model of Inflammatory Bowel Disease: Mice Deficient for the Multiple Drug Resistance Gene, mdr1a, Spontaneously Develop Colitis," Jour. of Immunology, 161:5733-5744, (1998).

Present et al., "Infliximab for the treatment of fistulas in patients with Crohn's Disease," New Eng. Jour. of Med., 340(18):1398-1405, (1999).

Raychaudhuri et al., "Fully mobilizing host defense: Building better vaccines," Nat. Biotechnol., 16:1025-1031, (1998).

Reddy, Bandaru, "Possible Mechanisms by Which Pro- and Prebiotics Influence Colon Carcinogenesis and Tumor Growth[1]," Amer. Soc. for Nut. Sci., pp. 1478S-1482S, (1999).

Rowland, Ian, "Toxicology of the Colon: Role of the Intestinal Microflora," Human Colonic Bacteria, pp. 155-174, (1995).

Rumney et al., "Effects of risk-associated human dietary macrocomponents on processes related to carcinogenesis in human-flora-associated (HFA) rats," Carcinogenesis, 14(1):79-84, (1993).

Saito et al., "Effects of Soybean Oligosaccharides on the Human Gut Microflora in In vitro Culture," Microbial Ecology in Health & Disease, 5:105-110, (1992).

Salminen et al., "Demonstration of safety of probiotics—a review," Int. Jour. of Food Microbiology, 44:93-106, (1998).

Sarath et al., "Protease assay methods," Proteolytic Enzymes, Chapter 3, pp. 25-55, (1989). (Previously cited as Gauthan et al.).

Sarem-Damerdji et al., "In vitro colonization ability of human colon mucosa by exogenous Lactobacillus strains," FEMS Microbiology Letters, 131:133-137, (1995).

Savage, D. "Interactions Between the Host and its Microbes," Microbial Ecology of the Gut, pp. 277-310, (1977).

Scardovi et al., "Genus Bifidobacterium, Bergey's Manual of Systemic Bacteriology," 2:1418-1434, (1986).

Schmitt et al., "The Immunostimulatory Function of IL-12 in T-Helper Cell Development and Its Regulation by TGF-$\beta$, IFN-$\gamma$ and IL-4," Chem. Immunology, 68:70-85, (1997).

Shanahan et al., "Immunosuppressive agents in inflammatory bowel disease: Current status and future prospects," Can J Gastroenterol, 8(6):383-387, (1994).

Shanahan, "Pathogenic mechanisms in inflammatory bowel disease," Gastrointestinal Function, 13:13-28, (1995).

Shanahan et al., "Grand Entry for Listeria," Gastroenterology, 112:1045-1046, (1997).

Shanahan, et al., "In vivo Primed Cytotoxic T Cells in Inflammatory Bowel Disease," Inflammatory Bowel Disease, Int'l Congress, pp. 101-106, (1988).

Shanahan, Fergus, "The Intestinal Immune System," Physiology of the Gastrointestinal Tract, pp. 643-684, (1994).

Shanahan et al., "Immunosuppressive agents in IBD: current status and future prospects." Inflammatory Bowel Disease, pp. 367-373, (1994).

Siitonen et al., "Effect of Lactobacillus GG Yoghurt in Prevention of Antibiotic Associated Diarrhoea," Annual Med., 22(1):57-59, (1990).

Singh et al., "Bifidobacterium longum, a lactic acid-producing intestinal bacterium inhibits colon cancer and modulates the intermediate biomarkers of colon carcinogenesis," Carcinogenesis, 18(4):833-841, (1997).

Stallmach et al., "Induction and modulation of gastrointestinal inflammation," Trends Immunology Today, 19(10):438-441, (1998).

Stanton et al., "Probiotic Cheese," Int. Dairy Journal, 8:491-496, (1998).

Steidler et al., "Mucosal Delivery of Murine Interleukin-2 (IL-2) and IL-6 by Recombinant Strains of Lactococcus lactis Coexpressing Antigen and Cytokine," Infection and Immunity, 66(7):3183-3189, (1998).

Tagg et al., "Bacteriocins of Gram-Positive Bacteria," Bacteriolocial Reviews, 40(3):722-756, (1976).

Takiguchi et al., "Effects of Fermented-Milk Administration on Fecal Microflora and Putrefactive Metabolites of Healthy Adults and Healthy Elderly Persons," Bifidus-Flores, Fructus et Semina 9, pp. 135-140, (1996).

Tancrede, C., "Role of Human Microflora in Health and Disease," Eur. J. Clin. Microbiol. Infect. Dis., 11(11):1012-1015, (1992).

Tannock, Gerald, "Effect of Dietary and Environmental Stress on the Gastrointestinal Microbiota," Human Intestinal Microflora in Health & Disease, pp. 517-539, (1983).

Thornton et al., "Bile tolerance and bile salt hydrolase activity of lactobacilli and bifidobacteria isolated from the human intestine," Gastroenterology, 108(4):A928, (1995).

Thornton et al., "Human Intestinal Probiotic Bacteria: Production of Antimicrobial Factors," Irish Jour of Med. Sci., 2 pages, (1993).

Thornton et al., "Towards an Understanding of the Survival Mechanisms Employed by the Health Promoting Commensal Flora of the Human Small Intestine," Irish Jour. of Med. Sci., p. 603, (1994).

Thornton et al., "Determination of stringent criteria essential to the survival/growth/colonisation of probiotic human intestinal tract bacteria," Book of Abstracts Eur. Comm. Biotech and Fair Programmes, p. 28, (1995). (Previously cited as Collins et al.).

Thornton et al., "The Production of a Novel Antimicrobial Substance by Human Intestinal Microflora," Irish Jour. of Med Sci, pp. 603-604, (1994).

Thornton, et al., "Bile Acid Tolerance and Deconjugating Activity of Lactobility," Irish Jour. of Med. Sci., 2 pages, (1994).

Toba et al., "Potential of Lactobacillus gasseri isolated from infact faeces to produce bacteriocin," Letters in Applied Microbiology, 12:228-231, (1991).

van Eys, Jan, "Nutrition and Neoplasia," Nutrition Reviews, 40(12):353-359, (1982).

Vaughan et al., "Identification and characterization of helveticin V-1829, a bacteriocin produced by Lactobacillus helveticus 1829," Journal of Applied Bacteriology, 73:299-308, (1992).

Vaughan et al., "Isolation from food sources, of lactic acid bacteria that produced antimicrobials," Journal of Applied Bacteriology, 76:118-123, (1994).

Veld et al., "Selection criteria for probiotic micro-organisms," International Congress and Symposium Series 219, pp. 27-36 (1996).

Wahl et al., "IFN-$\gamma$ Inhibits Inflammatory Cell Recruitment and the Evolution of Bacterial Cell Wall-Induced Arthritis," Journal of Immunology, 146(1):95-100, (1991).

Walker, Richard, "New strategies for using mucosal vaccination to achieve more effective immunization," Vaccine, 12:387-400, (1994).

Wu, et al., "Transfection of Ovarian Cancer Cells with Tumor Necrosis Factor-$\beta$ (TNF-$\beta$) Antisense mRNA Abolishes the Proliferative Response to Interleukin-1 (IL-1) but Not TNF-$\beta$," Gynecologic Oncology, 53:59-63, (1994). (Formerly cited as Meeker et al.).

Yang et al., "Genetics of Inflammatory Bowel Disease," Chapter 3, pp. 32-64, (1994).

Cong et al., "CD4+ T cells reactive to enteric bacterial antigens in spontaneously colitic C3H/HeJBir mice: increased T helper cell type 1 response and ability to transfer disease," J Exp Med, 187(6):855-64, (1998).

* cited by examiner

BIFIDOBACTERIUM IN THE TREATMENT OF INFLAMMATORY DISEASE

This is a Continuation of application Ser. No. 09/903,681 filed Jul. 13, 2000 (presently abandoned) which in turn is a Continuation of PCT/IE00/00008 filed Jan. 17, 2000.

INTRODUCTION

This invention relates to probiotic *Bifidobacterium* strains which have various applications in foodstuffs and in medicine. More particularly, the invention relates to probiotic strains of *bifidobacteria* which are capable of beneficially modifying and consequently alleviating observable symptoms in inflammatory disease.

Consumers are becoming increasingly aware of matters which may be necessary for maintenance of their environment, health and nutrition. In response, scientific research has focussed upon the roles that diet, stress, and modern medical practices (e.g. antibiotics and radiotherapy) may play in threatening human health. In particular, population dynamics shifting towards older societies are increasing the incidence of illnesses which may be caused by deficient or compromised microflora such as gastrointestinal tract (GIT) infections, constipation, irritable bowel syndrome (IBS), inflammatory bowel disease (IBD)—Crohn's disease and ulcerative colitis, food allergies, antibiotic-induced diarrhoea, cardiovascular disease, and certain cancers (e.g. colorectal cancer).

Probiotics have been defined as live microbial food supplements which beneficially affect the host by improving the intestinal microbial balance, or more broadly, as living micro-organisms, which upon ingestion in certain numbers, exert health effects beyond inherent basic nutrition. Cocktails of various micro-organisms, particularly species of *Lactobacillus* and *Streptococcus*, have traditionally been used in fermented dairy products to promote health.

In recent years the commercial manufacture and marketing of functional foods (foods which affect functions of the body in a targeted manner so as to bring about positive affects on physiology and nutrition), particularly probiotic (Acidophilus-Bifidus) yoghurts, has spread from the well-established Japanese niche market place into the lucrative and expanding European Union. While a number of probiotic bacteria of human origin are now being exploited commercially (e.g., L. acidophilus LA-1), many consumers, consumer organisations, and members of the scientific community are sceptical of such products and their publicised probiotic claims. The diary-food industry is therefore under considerable pressure to scientifically validate these new probiotic food products.

Criteria which have been suggested for the selection of potentially effective probiotic micro-organisms may be summarised as follows: human origin, non-pathogenic behaviour, resistance to technological processes (i.e., viability and activity in delivery vehicles), resistance to gastric acidity and bile toxicity, adhesion to gut epithelial tissue, ability to colonise the GIT, production of antimicrobial substances, ability to modulate immune responses, and the ability to influence metabolic activities (e.g., cholesterol assimilation, lactase activity, vitamin production) (Huis in't Veld J, Shortt C. Selection criteria for probiotic micro-organisms. In: Leeds, A. R., Rowland, I. R. eds. Gut Fora and Health— Past, Present and Future. London: The Royal Society of Medicine Press Ltd., 1996:19–26).

*Bifidobacteria* are one of several predominant culturable bacteria present in the colonic microflora.

The functions of endogenous *bifidobacteria* in the colon have not been completely elucidated. However, it is recognised that exclusively breast-fed infants have a reduced risk of diarrhoea compared with formula-fed infants. The fact that these infants have greater numbers of colonic *bifidobacteria* may in part explain this observed health advantage as the occupation of available niches in the GIT by large numbers of nonpathogenic *bifidobacteria* may help prevent bacterial infection. The pathogenesis of Crohn's disease is thought to be related to colonic bacterial microflora (Targan, S. and Shanahan, F. Inflammatory bowel disease: From bench to bedside. Williams and Wilkins 1994.) It has recently been found that patients suffering from active Crohn's disease have significantly less recoverable *bifidobacteria* in their faeces compared with healthy individuals. This reduction in *bifidobacteria* numbers was observed to be directly correlated with decreased levels of β-D galactosidase production and activity (Favier, C. et al, Dig. Dis. Sci. 1997;42:817–822). β-D galactosidase is an enzyme produced by *bifidobacteria*. These results support suggestions proposed in other studies that strains of *bifidobacteria* may play important roles in maintaining a balanced healthy intestinal microflora.

*Bifidobacteria* are considered to be probiotics as they are living organisms which exert healthy effects beyond basic nutrition when ingested in sufficient numbers. Numerous ingested *bifidobacteria* must reach the site of action in the gut in order to exert a probiotic effect. A minimum level of approximately $10^6$–$10^7$ viable *bifidobacteria* per gram intestinal contents has been suggested (Bouhnik, Y., Lait 1993: 73:241–247). There are reports in the literature which show that in vivo studies completed in adults and in infants indicate that some strains of *bifidobacteria* are capable of surviving passage through the gastrointestinal tract. Significant differences have been observed between the abilities of different *bifidobacteria* strains to tolerate acid and bile salts, indicating that survival is an important criterion for the selection of potential probiotic strains.

Ingestion of *bifidobacteria* can improve gastrointestinal transit.

Furthermore, indirect evidence in humans demonstrates that consuming milk fermented by *bifidobacteria* can lead to reduced levels of certain faecal enzymes such as β-D galactosidase implicated in the conversion of procarcinogens to carcinogens (Bouhnik Y. et at, Eur. J. Clin. Nutr. 1996;50: 269–273). Faecal-borne putrefaction metabolities such as p-cresol, indole and ammonia were also reduced when subjects consumed milk fermented by *Bifidobacrerium longum* and *S. thermophilus* (Takiguchi, R. et al. *Bifidus— Flores, Fructus et Semina* 1996;9:135–140).

Antimicrobial activity has been reported to be associated with *bifidobacteria*. Also, *bifidobacteria* have been shown to modulate various parameters of the immune system.

Mucosal inflammation in IL-10 deficient mice has been reported to be reduced by feeding the subject animals a preparation of lactic acid bacteria (Madsen, K. et al., Gastroenterol. 1997; 112:A1030.). Further studies completed in rats have demonstrated that ingestion of *bifidobacteria* can suppress aberrant crypt foci (early preneoplastic lesions) formation in the colon (Kulkarni, N. and Reddy, B. Proc. Soc. Experim. Biol. Med. 1994; 207; 278–283.) in addition to significant decreases in colon tumor incidence and in the numbers of tumors present (Singh, J. et al Carcinogenesis 1997; 18:833–841).

There is an on-going search for probiotic strains with particular beneficial effects on nutrition and therapy and on health generally.

Statements of Invention

The invention provides a strain of *Bifidobacterium* isolated from resected and washed human gastrointestinal tract which is significantly immunomodulatory following oral consumption in humans.

The strain of *Bifidobacterium* preferably effects changes in an immunological marker when introduced into a system comprising cells which interact with the immune system and cells of the immune system. Preferably the cells which interact with the immune system are epithelial cells. Preferably the immunological marker is a cytokine, especially TNFα.

In a preferred embodiment the cells which interact with the immune system and the immune system cells are of matched origin.

The cells which interact with the immune system are of gastrointestinal, respiratory or genitourinary origin.

The cells of the immune system are preferably of gastrointestinal, respiratory or genitourinary origin. The invention also provides a strain of *Bifidobacterium longum infantis* isolated from resected and washed human gastrointestinal tract which is significantly immunomodulatory following oral consumption in humans.

The strain of *Bifidobacterium* which has significant anti-inflammatory effect following oral consumption in humans.

The strain of *Bifidobacterium* is preferably isolated from resected and washed human gastrointestinal tract which is capable of combating the effects of inflammatory bowel disease, said capability being maintained in the presence of physiological concentrations of human bile and human gastric juice. The capability of combating the effects of inflammatory bowel disease is measured by measuring a reversal of a wasting disease induced in severe combined immunodeficient recipient mice (SCID) which have been administered purified $CD4^+$, $CD45RB^{high}$ T cells.

The capability of the strain of *Bifidobacterium longum infantis* to combat the effects of inflammatory bowel disease can also be measured by measuring the reduction in colonic inflammation in IL-10 deficient mice (IL-$10^+$ 129 Svex strain) following administration of one or more of the strains of *Bifidobacterium longum infantis* according to the invention alone or in combination with a strain of *Lactobacillus salivarius* as hereinafter defined.

Interleukin 10 (IL-10) is an important regulatory cytokine that supresses effector functions of macrophage/monocytes, T helper 1 (Th1) cells, and natural killer cells. In addition, IL-10 augments proliferation and differentiation of B cells. Murine models lacking the IL-10 gene spontaneously develop inflammatory bowel disease and gastrointestinal tumors. The gastrointestinal flora have been implicated in the pathogenesis of these disease states as germ free animals do not develop disease.

The strain of *Bifidobacterium* preferably has inhibitory activity against a broad range of Gram positive and Gram negative bacteria.

Preferably the strain of *Bifidobacterium* exhibits a broad-spectrum of activity against bacteria including *Staphylococcus, Pseudomonas, Coliform* and *Bacillus* species.

In a particular aspect the invention provides strain of *Bifidobacterium longum infanis* UCC35624 or mutant or variant thereof.

A deposit of *Bifidobacterium longum infantis* strain UCC 35624 was made at the National Collections of Industrial and Marine Bacteria Limited (NCIMB) at Ferguson Building, Craibstone Estate, Bucksburn, Aberdeen AB21 9YA, UK Jan. 13, 1999 and accorded the accession number NCIMB 41003.

In one embodiment the mutant is a genetically modified mutant.

In one embodiment the variant is a naturally occurring variant of *Bifidobacterium longum infantis* UCC35624.

The strain of *Bifidobacterium* may be in the form of viable cells. Alternatively the strain of *Bifidobacterium* is in the form of non-viable cells.

The invention also provides an antimicrobial agent obtained from a strain of *Bifidobacterium* of the invention which is antagonistic to the growth of other organisms.

In a further aspect the invention provides a formulation which comprises a strain of *Bifidobacterium* of the invention.

The formulation may comprise two or more strains of *Bifidobacterium*.

The formulation may include another probiotic material. Alternatively or additionally the formulation includes a prebiotic material.

The formulation may which include a strain of *Lactobacillus salivarius*.

The strain of *Lactobacillus salivarius* may be in the form of viable cells or in the form of non-viable cells.

The *Lactobacillus salivarius* is preferably isolated from resected and washed human gastrointestinal tract, the *Lactobacillus salivarius* being significantly immunomodulatory following oral consumption in humans. Preferably the strain of *Lactobacillus salivarius* is isolated from resected and washed human gastrointestinal tract which inhibits a broad range of Gram positive and Gram negative micro-organisms.

In a preferred embodiment the strain of *Lactobacillus salivarius* secretes a product having antimicrobial activity into a cell—free supernatant, said activity being produced only by growing cells and being destroyed by proteinase K and pronase E, the inhibitory properties of said strain and its secretory products being maintained in the presence of physiological concentration of human bile and human gastric juice.

Such strains of *Lactobacillus salivarius* are disclosed in WO 98/35014.

Ideally the strain of *Lactobacillus salivarius* is *Lactobacillus salivarius* strain UCC 118 or a mutant or variant thereof. The mutant is a genetically modified mutant.

The variant may be a naturally occurring variant of *Lactobacillus salivarius*.

A deposit of *Lactobacillus salivarius* strain UCC 118 was made at the National Collections of Industrial and Marine Bacteria Limited (NCIMB) at Ferguson Building, Craibstone Estate, Bucksbum, Aberdeen AB21 9YA, UK on Nov. 27, 1996 and accorded the accession number NCIMB 40829.

Preferably the formulation includes an ingestable carrier. The ingestable carrier may be a pharmaceutically acceptable carrier such as a capsule, tablet or powder.

The ingestable carrier may be a food product such as acidified milk, yogurt, frozen yoghurt, milk powder, milk concentrate, cheese spreads, dressings or beverages.

The formulation may comprise a protein and/or peptide, in particular proteins and/or peptides that are rich in glutamine/glutamate, a lipid, a carbohydrate, a vitamin, mineral and/or trace element.

In one embodiment the *Bifidobacterium* is present at more than $10^6$ cfu per gram of delivery system.

In another embodiment the formulation includes an adjuvant.

The formulation may include a bacterial component. The formulation may alternatively or additionally include a drug entity. The formulation may also include a biological compound.

The formulation may be in a form for oral immunisation.

The invention further provides a strain of *Bifidobacterium* or a formulation thereof for use in foodstuffs.

In another aspect the invention provides a strain of *Bifidobacterium* or a formulation thereof for use as a medicament.

The strain or formulation may be for use in the prophylaxis and/or treatment of undesirable inflammatory activity.

The strain or formulation may be for use in the prophylaxis and/or treatment of undesirable gastrointestinal inflammatory activity such as inflammatory bowel disease eg. Crohns disease or ulcerative colitis, irritable bowel syndrome, pouchitis or post infection colitis.

The undesirable inflammatory activity may be due to cancer.

In addition the strain or formulation may be for use in the prophylaxis and/or treatment of gastrointestinal cancer(s).

The strain or formulation may be used for the prophylaxis of cancer. Further, the strain or formulation may be for use in the prophylaxis and/or treatment of systemic disease such as rheumatoid arthritis.

The strain or formulation may be for use in the prophylaxis and/or treatment of autoimmune disorders due to undesirable inflammatory activity.

The strain or formulation may be for use in the prophylaxis and/or treatment of cancer due to undesirable inflammatory activity.

The strain or formulation may be for use in the prophylaxis and/or treatment of diarrhoeal disease due undesirable inflammatory activity, such as *Costidium difficile* associated diarrhoea, Rotavirus associated diarrhoea or post infective diarrhoea.

DETAILED DESCRIPTION

Figure 1:
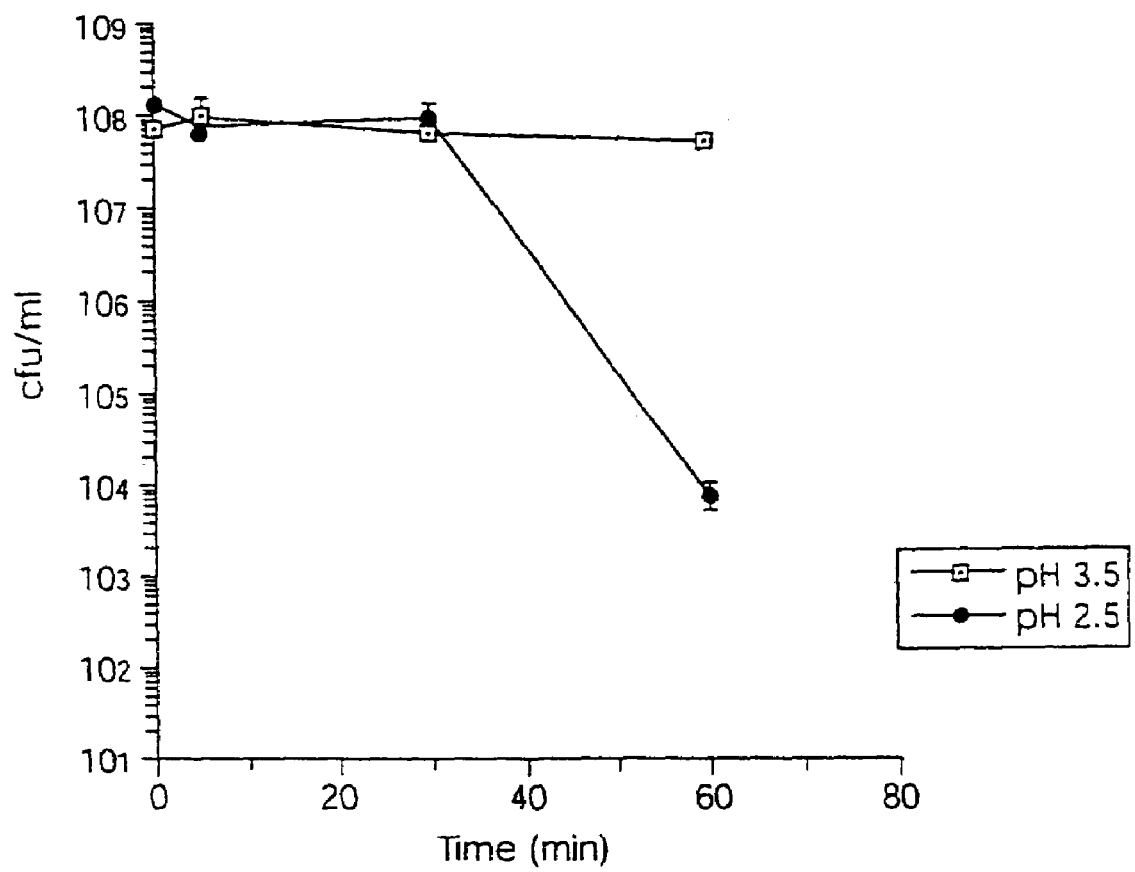
FIG. 1 is a graph of cfu/ml versus time for *Bifidobacterium longum infantis* strain 35612 as described in Example 2.

We have isolated strains of probiotic bacteria which are capable of beneficially modifying and consequently alleviating observable symptoms in inflammatory disorders. These strains and the formulations prepared may be used in a variety of foodstuffs and medicaments to combat the effect of inflammatory disorders.

In vivo and in vitro studies were carried out using the probiotic bacteria strains. It was found that humans fed with yoghurt containing *Bifidobacterium longum infantis* UCC35624 show marked decreases in their systemic levels of IL-8. This strain may therefore have potential application in the treatment of a range of inflammatory disorders, particularly if used in combination with current anti-inflammatory therapies, such as non-steroid anti-inflammatory drugs (NSAIDs) or Infliximab.

The consumption of *Bifidobacterium longum infantis* by SCID mice was also examined. While this experiment significantly attenuated inflammatory activity, mice consuming *Bifidobacterium longum infantis* retained solid stools while control mice suffered from diarrhoea. This anti-diarrhoeal effect could be related to the anti-inflammatory activity of this invention, possibly mediated via cAMP modulation.

It is unknown whether intact bacteria are required to exert an anti-inflammatory effect or if individual active components of the invention can be utilised alone. Proinflammatory components of certain bacterial strains have been identified. The proinflammatory effects of gram-negative bacteria are mediated by lipopolysaccharide (LPS). LPS alone induces a proinflammatory network, partially due to LPS binding to the CD14 receptor on monocytes. It is assumed that components of probiotic bacteria possess antiinflammatory activity, due to the effects of the whole cell. Upon isolation of these components, pharmaceutical grade manipulation is anticipated.

The general use of *Bifidobacterium longum infantis* UCC35624 is in the form of viable cells. However, it can also be extended to non-viable cells such as killed cultures or compositions containing beneficial factors expressed by *Bifidobacterium longum infantis* UCC35624. This could include thermally killed micro-organisms or microorganisms killed by exposure to altered pH or subjection to pressure. With non-viable cells product preparation is simpler, cells may be incorporated easily into pharmaceuticals and storage requirements are much less limited than viable cells. *Lactobacillus casei* YIT 9018 offers an example of the effective use of heat killed cells as a method for the treatment and/or prevention of tumour growth as described in U.S. Pat. No. 4,347,240.

The invention will be more clearly understood from the following Examples.

EXAMPLE 1

Isolation of Probiotic Bacteria

Appendices and sections of the large and small intestine of the human G.I.T., obtained during reconstructive surgery, were screened for probiotic bacterial strains as shown in Table 1.

TABLE 1

Gastrointestinal tract tissue samples screened for the presence of probiotic bacteria

| Sample | Location |
|---|---|
| A | Ileum |
| B | Colon |
| C | Ileal-caecal region |
| D | Appendix |
| E | Appendix |
| F | Ileum |
| G | Ileal-caecal region |

All samples were stored immediately after surgery at −80° C. in sterile containers. Frozen tissues were thawed, weighed and placed in cysteinated (0.05%) one quarter strength Ringers' solution. Each sample was gently shaken to remove loosely adhering microorganisms (termed—wash 'W'). Following transfer to a second volume of Ringers' solution, the sample was vortexed for 7 min to remove tightly adhering bacteria (termed—Sample 'S'). In order to isolate tissue embedded bacteria, samples A, B and C were also homogenised in a Braun blender (termed—homogenate 'H'). The solutions were serially diluted (dilution $10^{-1}$ from a wash sample was labelled W1, dilution $10^{-2}$ was labelled W2 and the same labelling system was used for the 'S' and 'H' samples) and spread-plated (100 µl) on to the following agar media: RCM (reinforced clostridial media) and RCM adjusted to pH 5.5 using acetic acid; TPY (typticase, peptone and yeast extract), Chevalier, P. et al., (1990) *J. Appl. Bacteriol* 68, 619–624). MRS (deMann, Rogosa and Sharpe); ROG (acetate medium (SL) of Rogosa); LLA (Liver-lactose agar of Lapiere); BHI (brain heart infusion agar); LBS (*Lactobacillus* selective agar) and TSAYE (tryptone soya agar supplemented with 0.6% yeast extract). All agar media was supplied by Oxoid Chemicals with the exception of TPY agar. Plates were incubated in anaerobic jars (BBL, Oxoid) using $CO_2$ generating kits (Anaerocult A, Merck) for 2–5 days at 37° C.

Gram positive, catalase negative rod-shaped or bifurcated/pleomorphic bacteria isolates were streaked for purity on to complex non-selective media (TPY). Isolates were routinely cultivated in TPY medium unless otherwise stated at 37° C. under anaerobic conditions. Presumptive *Bifidobacteria* species were stocked in 40% glycerol and stored at −20° and −80° C.

Fermentation End-Product Analysis

Metabolism of the carbohydrate glucose and the subsequent organic acid end-products were examined using an LKB Bromma, Aminex HPX-87H High Performance Liquid Chromatography (HPLC) column. The column was maintained at 60° C. with a flow rate of 0.6 ml/min (constant pressure). The HPLC buffer used was 0.01 N $H_2SO_4$. Prior to analysis, the column was calibrated using 10 mM citrate, 10 mM glucose, 20 mM lactate and 10 mM acetate as standards. Cultures were propagated in modified MRS broth for 1–2 days at 37° C. anaerobically. Following centrifugation for 10 min at 14,000 g, the supernatant was diluted 1:5 with HPLC buffer and 200 µl was analysed in the HPLC. All supernatants were analysed in duplicate.

Biochemical and Physiological Characterisation

Biochemical and physiological traits of the bacterial isolates were determined to aid identification. Nitrate reduction, indole formation and expression of β-galactosidase activity were assayed. Growth at both 15° C. and 45° C. and protease activity on gelatin were determined. Growth characteristics of the strains in litmus milk were also assessed.

Antibiotic Sensitivity Profiles

Antibiotic sensitivity profiles of the isolates were determined using the 'disc susceptibility' assay. Cultures were grown up in the appropriate broth medium for 24–48 h, spread-plated (100 µl) onto agar media and discs containing known concentrations of the antibiotics were placed onto the agar. Strains were examined for antibiotic sensitivity after 1–2 days incubation at 37° C. under anaerobic conditions. Strains were considered sensitive if zones of inhibition of 1 nm or greater were seen.

Isolation of *Bifidobacteria* sp.

Seven tissue sections taken from the human G.I.T. were screened for the presence of strains belonging to the *Bifidobacterium* genus. There was some variation between tissue samples as follows. Samples A (ileum) and E (appendix) had the lowest counts with approximately $10^2$ cells isolated per gram of tissue. In comparison, greater than $10^3$ cfu/g tissue were recovered from the other samples. Similar numbers of bacteria were isolated during the 'wash' and 'sample' steps with slightly higher counts in the 'sample' solutions of F (ileum) and G (ileal-caecal). Of those screened for tightly-adhering bacteria (homogenised), C (ileal-caecal) was the only tissue section that gave significant counts.

During the screening of some tissue sections, for example C and B, there was not a direct correlation between counts obtained during a dilution series. This would indicate that some growth factors, either blood or tissue derived were being provided for the growth of the fastidious bacteria in the initial suspension which was subsequently diluted out.

Strain Selection and Characterisation

Approximately fifteen hundred catalase negative bacterial isolates from different samples were chosen and characterised in terms of their Gram reaction, cell size and morphology, growth at 15° C. and 45° C. and fermentation end-products from glucose. Greater than sixty percent of the isolates tested were Gram positive, homofermentative cocci arranged either in tetrads, chains or bunches. Eighteen percent of the isolates were Gram negative rods and heterofermentative coccobacilli.

The remaining isolates (twenty-two percent) were predominantly homofermentative coccobacilli. Thirty eight strains were characterised in more detail-13 isolates from G; 4 from F; 8 from D; 9 from C; 3 from B and 1 from E. All thirty eight isolates tested negative both for nitrate reduction and production of indole from tryptophan.

Antibiotic Sensitivity Profiles

Antibiotics of human clinical importance were used to ascertain the sensitivity profiles of selected *bifidobacteria*. The *bifidobacteria* tested were sensitive to ampicillin, amoxycillin ceftaxime, ceftriaxone, ciprofloxacin, cephradine, rifampicin, amikacin, gentamicin and chloramphenicol. They were also resistant to netilmicin, trimethoprim, nalidixic acid, cefiroxime, vancomycin and tetracycline.

EXAMPLE 2

Acid Resistance

The first line of host defence that a micro-organism reaches following human consumption is gastric acid in the stomach. A key factor influencing bacteria is survival in gastric juice. The survival and growth of *Bifidobacterium longum infantis* strains 35612 and 35624 in a low pH environment were examined. The strains were routinely cultured in trypticase-peptone-yeast extract (TPY) medium at 37° C. under strict anaerobic conditions (BBL Gas jars using the Merck Anaerocult A gas pak system) for 12–24 h. Human gastric juice was obtained from healthy subjects by aspiration through a nasogastric tube (Mercy Hospital, Cork, Ireland). It was immediately centriguned at 13,000 g for 30 min. to remove all solid particles, sterilised through 0.45 μm filters and 0.2 μm filters and stored at 4° C. The pH and pepsin activity were measured prior to experimental use. Pepsin activity was measured using the quantitative haemoglobin assay (Guantam, S. and R. S. de la Motte. 1989. Proteolytic enzymes, a practical approach. Chapter 3. R. J. Beynon and J. S. Bond (eds.), IRL Press, Oxford University Press; Dawson, R. M. 1969. pH and buffers. In Data for Biochemical Research p 138. R. M. Dawson, D. C. Elliot and K. M. Jones (eds.), Clarendon Press, Oxford). Survival of the strains at low pH in vitro was investigated using the following assays:

(a) Cells were harvested from fresh overnight cultures, washed twice in phosphate buffer (pH 6.5) and resuspended in MRS broth adjusted to pH 3.5, 3.0, 2.5 and 2.0 (with 1N HCl) to a final concentration of approximately $10^6$ cfu/ml. Cells were incubated at 37° C. and survival measured at intervals of 5, 30, 60 and 120 min. using the plate count method.

Figure 2:
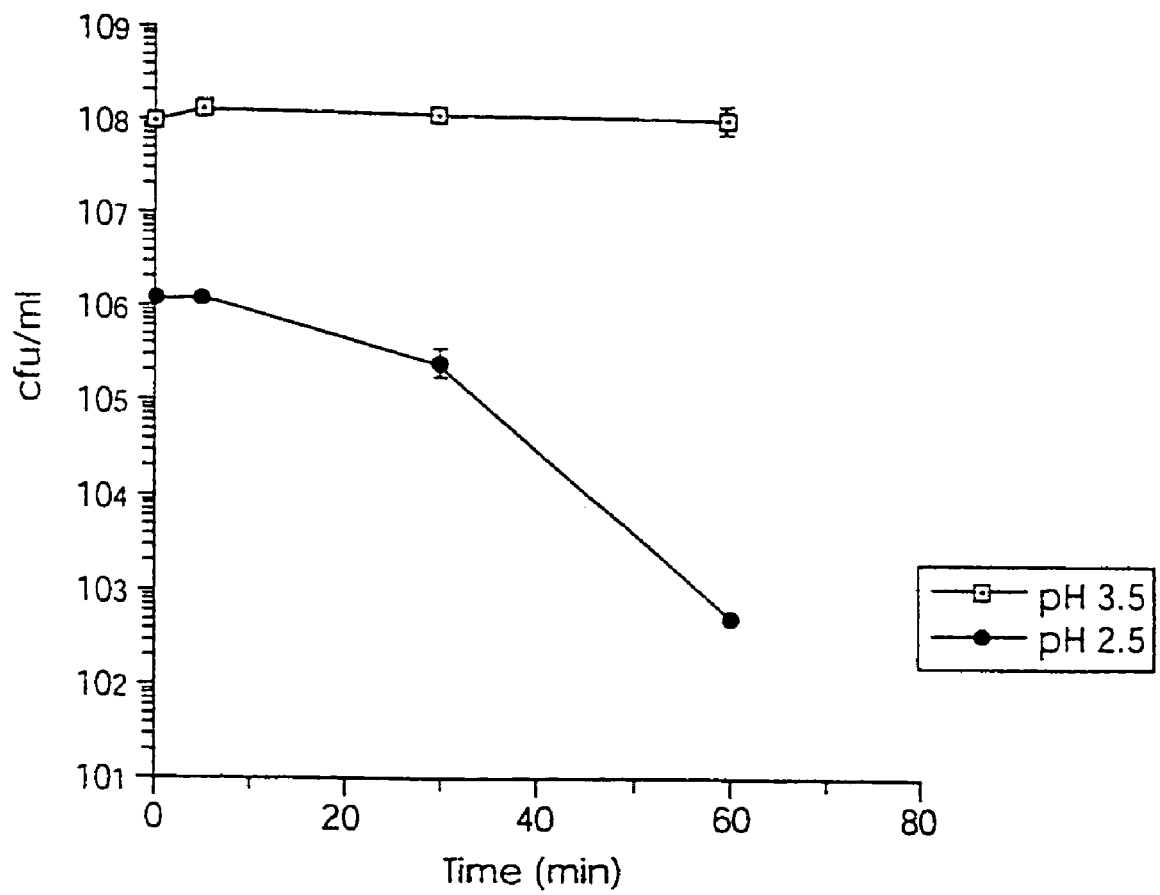
FIG. 2 is a graph of cfu/ml versus time for *Bifidobacterium longum infantis* strain 35624 as described in Example 2.

The strains survived with no loss of viability at pH 3.5. At pH 2.5 there was a 3 log reduction over the 60 min. incubation period as depicted in FIGS. 1 and 2.

Survival of Strains of *Bifidobacterium* in Human Gastric Juice

Fresh overnight cultures were harvested, washed twice in buffer (pH 6.5) and resuspended in human gastric juice to a final concentration of $10^6$ cfu/ml. Survival was monitored over a 30–60 min incubation period at 37° C. The experiment was performed using gastric juice at pH 1.2 (unadjusted) and pH 2.0 and 2.5 (adjusted using 1N NaOH).

Survival of the strains was increased in gastric juice at pH 2.0, when compared with gastric juice at pH 1.2. After 30 min incubation no viable cells were recovered at either pH as shown in Table 2.

TABLE 2

Survival of *Bifidobacterium* sp. in human gastric juice*

| STRAIN | pH | 0 | 5 | 30 | 60 |
|---|---|---|---|---|---|
| 35612 | 1.2 | 7.56 | 0.00 | 0.00 | 0.00 |
|  | 2.0 | 6.27 | 6.31 | 2.88 | 0.00 |
| 35624 | 1.2 | 5.96 | 4.18 | 0.00 | 0.00 |
|  | 2.0 | 6.33 | 6.32 | 0.00 | 0.00 |
| 35652 | 1.2 | 6.16 | 3.78 | 0.00 | 0.00 |
|  | 2.0 | 8.45 | 8.40 | 3.45 | 0.00 |
| 35648 | 1.2 | 6.00 | 0.00 | 0.00 | 0.00 |
|  | 2.0 | 7.89 | 6.45 | 0.00 | 0.00 |
| 35687 | 1.2 | 6.68 | 0.00 | 0.00 | 0.00 |
|  | 2.0 | 8.75 | 8.77 | 3.34 | 0.00 |
| BO | 2.0 | 8.41 | 8.56 | 8.42 | 8.43 |
| 10 | 2.0 | 8.39 | 8.56 | 4.64 | 0.00 |
| 6.3 | 2.0 | 8.75 | 8.75 | 8.29 | 8.42 |
| B. longum 6 | 2.0 | 8.15 | 8.02 | 0.00 | 0.00 |

*survival expressed as $\log_{10}$ cfu/ml

EXAMPLE 3

Bile Resistance

In the evaluation of the effectiveness of using lactic acid bacteria as beneficial members of the gastrointestinal tract, it is considered that resistance to bile acids is an important biological strain characteristic required for survival in this hostile environment and in addition they must not impinge on the health of the host by producing toxic compounds such as deoxycholic (DCA) and lithocholic acid (LCA) which have been implicated in a number of cytotoxic phenomena.

A number of *Bifidobacterium longum infantis* strains were streaked onto TPY agar plates supplemented with porcine bile (B-8631, Sigma Chemical Co. ltd., Poole) at concentrations of 0.3, 0.5, 1.0, 1.5, 5.0 and 7.5% (w/v) (Legrand-Defretin, R. et al., Lipids 1991; 26 (8), 578–583). Porcine bile is the closest in composition to human bile with respect to bile salt/cholesterol and phospholipid/cholesterol ratios. Plates were incubated at 37° C. under anaerobic conditions and growth was recorded after 24–48 h. Strain 35624 was found to be strongly bile resistant and grew to confluence at up to 55 porcine bile as shown in Table 3.

TABLE 3

Growth of *Bifidobacterium* sp. isolates in the presence of porcine bile

| STRAIN | % (w/v) PORCINE BILE | | | | | | |
|---|---|---|---|---|---|---|---|
|  | 0.0 | 0.3 | 0.5 | 1.0 | 1.5 | 5.0 | 7.5 |
| 34612 | + | − | − | − | − | − | − |
| 35624 | + | + | + | + | + | + | − |
| 35652 | + | − | − | − | − | − | − |
| 35658 | + | + | + | + | − | − | − |
| 35687 | + | − | − | − | − | − | − |

−, no growth;
+, confluent growth

Human bile was obtained from several human gall bladders and sterilised at 80° C. for 10 min. The bile acid composition of human bile was determined using reverse phase High Performance Liquid Chromatography (HPLC) in combination with a pulsed amperometric detector according to the method of Dekker, R. R. et al., Chromatogaphia, 1991, 31 (11/12), 255–256. Human bile was added at a concentration of 0.3% (v/v). Freshly streaked cultures were examined for growth after 24 and 48 h.

Strain 35624 was capable of growth in the presence of physiologically relevant human bile (0.3% (v/v)).

Growth of the strains was examined in the presence of individual conjugated and deconjugated bile acids. Under physiological conditions bile acids are often found as sodium salts. The strains were screened for growth on TPY agar containing the conjugated and deconjugated sodium salts of each of the following bile acids.

(a) conjugated form: glycocholic acid (GCA); glycodeoxycholic acid (GDCA); and glycochenodeoxycholic acid (GCDCA);

(b) deconjugated form: lithocholic acid (LCA); chenodeoxycholic acid (CDCA); deoxycholic acid (DCA) and cholic acid (CA). For each bile acid concentrations of 1, 3 and 4 mM were used. Growth was recorded after 24 and 48 h anaerobic incubation.

The five strains studied grew on agar medium supplemented with 5 mM GCA and GCDCA and on agar medium supplemented with 1 mM GDCA as shown in Table 4. Strain 35624 was resistant to concentrations of 5 mM LCA (data not shown) and strains 35612 and 35624 were capable of growth at concentrations of 5 mM CA as shown in Table 5. No growth was observed in the presence of 1 mM CDCA (data not shown).

TABLE 4

Growth of *Bifidobacterium* sp. isolates in the presence of glycine-conjugated bile acids

| | BILE ACIDS (mM) | | | | | | | | | | | |
|---|---|---|---|---|---|---|---|---|---|---|---|---|
| | GCDCA | | | | GDCA | | | | GCA | | | |
| STRAIN | 0 | 1 | 3 | 5 | 0 | 1 | 3 | 5 | 0 | 1 | 3 | 5 |
| 35612 | + | + | + | + | + | + | + | + | + | + | + | + |
| 35624 | + | + | + | + | + | + | + | + | + | + | + | + |
| 35652 | + | + | + | + | + | + | + | + | + | + | + | + |
| 35658 | + | + | + | + | + | + | + | + | + | + | + | + |
| 35687 | + | + | + | + | + | + | + | + | + | + | + | + |

−, no growth;
+, confluent growth
GCDCA, glycochenodeoxycholic acid;
GDCA, glycodeoxycholic acid;
CGA, glycocholic acid.

TABLE 5

Growth of *Bifidobacterium* sp. isolates in the presence of unconjugated cholic acid (CA)

| | CHOLIC ACID (mM) | | | |
|---|---|---|---|---|
| STRAIN | 0 | 1 | 3 | 5 |
| 35612 | + | + | + | + |
| 35624 | + | + | + | + |
| 35652 | + | + | − | − |
| 35658 | + | + | − | − |
| 35687 | + | + | − | − |

−, no growth;
+, confluent growth

EXAMPLE 4

Antimicrobial Activity

*Bifidobacterium* species exert inhibitory effects on other bacteria by excluding long term colonisation by invasive pathogens. Their antagonistic activity is due to the production of acetic and lactic acid though fermentation (Scardovi, V. (1986) *Bifidobacterium* in Bergey's Manual of systemic bacteriology, Vol. 2. Eds. Sheath, P. H., Main, N. S., Sharpe, M. and Holdt, J. G., Williams and Wilkins Publishers, Baltimore M.D., p1418). Very few reports exist on the production of antimicrobial compounds other than acids (Anand, S. K. et al. Cult. Dairy Prods. 1985; J. 2, 21–23). Bacteriocins and other compounds may influence the survival of a bacterium in an ecological niche and allow them to effectively dominate fermenting ecosystems. Such a feature is a good trait for a probiotic strain.

The inhibitory spectra of various *bifidobacterial* strains was determined by the method of Tagg et al. (Tagg. J. R. et al. Bacteriol. Rev. 1976; 40, 722–756). Cell free supernatant was assayed for inhibitory activity against a wide range of Gram positive and Gram negative micro-organisms. Overlays of each indicator were prepared on agar plates and allowed to dry. Spots (5 ml) of cell free supernatant were placed on the seeded plates, allowed to dry and the plates were incubated overnight.

It was observed that the strains were inhibitory to a wide range of *Staphylococcus, Pseudomonas, Coliform* and *Bacillus* sp. when testes on TPY medium. Zones of inhibition of up to 4.4 mm were recorded against *Pseudomonas* and *Staphylococcus* and up to 7.0 mm surrounding *Bacillus* sp. as shown in Tables 6 and 7. However, when the deferred assays were performed on buffered TPY medium zones of inhibition were not observed against any indicator strain. Therefore, inhibition appeared to be solely due to the presence of acid produced by the *bifidobacteria*.

TABLE 6

Inhibition of *Staphylococcus* strains by *Bifidobacterium* sp. on unbuffered medium*

| | B. longum 1 | B. longum 9 | B. longum 10 | 63 | 35612 | 35624 | 35652 | 35658 | 35675 | 35678 | 35687 |
|---|---|---|---|---|---|---|---|---|---|---|---|
| S. aureus MHS | 1.5 | 2 | 1.5 | 3.5 | 1.5 | 1 | 2 | 2 | 1 | 2.5 | 1.5 |
| S. aureus HC | 1.5 | 1.5 | 2 | 2.5 | 2 | 1.5 | 2.5 | 2 | 1.5 | 1.5 | 2 |
| S. aureus 771 | 1.5 | 3 | 1.5 | 3 | 2 | 2 | 2.5 | 2 | 3 | 2 | 3.5 |
| S. aureus 949 | 2 | 3.5 | 2.5 | 2 | 3 | 3.5 | 3 | 2.5 | 3.5 | 3.5 | 2.5 |
| S. aureus 1018 | 1 | 3.5 | 1.5 | 1.5 | 2 | 3.5 | 1 | 3 | 3.5 | 2.5 | 2 |
| S. aureus 1502 | 1.5 | 3.5 | 1 | 2 | 2.5 | 2.5 | 1.5 | 3 | 4 | 2.5 | 1.5 |
| S. aureus 1505 | 3 | 4 | 3 | 2.5 | 2.5 | 3 | 2.5 | 4.5 | 5.5 | 5 | 5.5 |
| S. aureus 1511 | 1 | 3.5 | 2 | 1.5 | 2 | 2.5 | 3 | 3.5 | 4 | 2.5 | 3 |
| S. aureus 1522 | 1.5 | 3 | 2.5 | 1 | 2.5 | 1.5 | 2.5 | 2.5 | 3.5 | 3.5 | 3 |
| S. aureus 1499 | 1.5 | 3.5 | 1.5 | 1.5 | 2 | 2 | 3 | 2 | 3.5 | 3.5 | 1.5 |
| S. aureus 1963 | 2 | 3 | 2 | 2.5 | 3.5 | 3.5 | 3.5 | 3.5 | 2.5 | 3 | 2.5 |
| S. aureus PRMM | 1 | 3.5 | 1 | 1.5 | 1 | 3.5 | 2 | 2 | 3 | 2 | 2.5 |

TABLE 6-continued

Inhibition of Staphylococcus strains by Bifidobacterium sp. on unbuffered medium*

| | B. longum 1 | B. longum 9 | B. longum 10 | 63 | 35612 | 35624 | 35652 | 35658 | 35675 | 35678 | 35687 |
|---|---|---|---|---|---|---|---|---|---|---|---|
| S. albus | 1 | 2 | 1.5 | 1 | 2 | 2.5 | 2 | 1.5 | 2 | 1.5 | 1 |
| S. carnosus | 1 | 1.5 | 2 | 2.5 | 2.5 | 2.5 | 2 | 2.5 | 2 | 1.5 | 1 |

*values given are radii of inhibition zones in mm (distance from edge of producer colony to the edge of zone of inhibition)

TABLE 7

Inhibition of Pseudomonas and Bacillus strains by Bifidobacterium sp. on unbuffered medium*

| | B. longum 1 | B. longum 9 | B. longum 10 | 63 | 35612 | 35624 | 35652 | 35658 | 35675 | 35678 | 35687 |
|---|---|---|---|---|---|---|---|---|---|---|---|
| P. fluorescens HC. | 1 | 2.5 | 1.5 | 1 | 1.5 | 2 | 3 | 2 | 1.5 | 2 | 2.5 |
| P. fluorescens MHP | 1.5 | 4.5 | 3.5 | 2 | 2.5 | 3.5 | 2.5 | 2.5 | 3.5 | 2 | 4 |
| P. fluorescens DW | 1.5 | 4 | 4 | 3.5 | 2.5 | 3.5 | 2.5 | 4.5 | 5.5 | 3.5 | 5 |
| B. cereus | 3 | 3 | 5 | 3 | 4 | 4 | 3.5 | 5 | 6 | 4.5 | 5.5 |
| B. subtilis | 2 | 2.5 | 5 | 2 | 3 | 6 | 3 | 6 | 7 | 3 | 6 |
| B. circulans | 1 | 2 | 4 | 1.5 | 2.5 | 1.5 | 2 | 3.5 | 4.5 | 2 | 4.5 |
| B. thuringensis | 2.5 | 3.5 | 5 | 3 | 3.5 | 4.5 | 4 | 5.5 | 6.5 | 4.5 | 5.5 |

*values given are radii of inhibition zones in mm (distance from edge of producer colony to the edge of zone of inhibition)

EXAMPLE 5

Murine Feeding Trial to Investigate the Ability of *Lactobacillus salivarius* subsp. *Salivarius* UCC 118 and *Bifidobacteria longum infantis* 35624 to Alleviate the Symptoms of Inflammatory Bowel Disease (IBD)

Background

A number of mouse models have recently been generated by either genetic or immunological means to study the mechanisms of IBD. One of these models involves the transfer of spleen or lymph node-derived $CD4^+$ T lymphocytes from normal mice into severe combined immunodeficient recipient mice (SCID). It has been demonstrated that mice who receive purified $CD4^+$, $CD45RB^{high}$ T cells develop a wasting disease characterised by chronic intestinal inflammation which is more severe in the colon. In this study a control group of SCID mice was injected with $CD4^+$ $CD45RB^{high}$ and the mice developed a progressive wasting disease including hunched over appearance, piloerection of the coat, diarrhoea, weight loss and macro and microscopic colon damage. A feeding trail was set up administering UCC 118 and strain 35624 (also referred to herein as UCC 35624) to determine if the symptoms of IBD could be modified in this model.

Bacterial Strains

*Lactobacillus salivarius* subsp. *Salivarius* UCC 118 and *Bifidobacterium longum infantis* UCC 35624 were isolated from the ileal-caecal region of an adult human as described in Example 1. In this example, spontaneous rifampicin and streptomycin resistant derivatives of the strains were generated by plating cells, previously grown overnight and subsequently washed in quarter strength Ringer's solution on MRS and TPY agar containing 50 μg/ml rifampicin (Sigma) respectively and MRS containing 400 μg/ml streptomycin (Sigma). Plates were incubated for 2 days at 37° C. anaerobically. The resulting antibiotic resistant derivatives were determined to be otherwise phenotypically similar to the parent strain. This selectable trait enabled the strains to be readily enumerated following gut transit.

Animals and Maintenance

Donor mice (C57BL/6×BALB/c) F1 were purchased from Simosen Laboratories (Gilroy, Calif.) and maintained at the University of California—Los Angeles vivarium in ventilated cage racks (Thoren caging systems, Hazelton, Pa.) under specific pathogen free (SPF) conditions. CB-17 SCID mice were bred in ventilated cage racks originally obtained from the University of California—Los Angeles SCID core facility. The nice were reduced flora (RF) mice rather than germ free and acting as the recipient mice (Aranda R. et al. J. of Immunol. 1997; 158(7), 3464–3473).

Eight week old, female CB-17 (SCID) mice were housed in pairs in filter top cages in ventilated racks. The mice were divided into four groups Group A: consumed 10% skim milk, control; Group B: consumed *Lactobacillus salivarius* UCC 118, Group C: consumed *Lactobacillus salivarius* UCC 118 and *Bifidobacterium longum* UCC 35624 9 (1:1 ratio); Group D: consumed *Bifidobacterium longum* UCC 35624. UCC 118 and UCC 35624 which were grown overnight in MRS broth and MRS broth supplemented with 0.05% cysteine (Sigma) respectively, were washed in PBS, resuspended in skim milk (10% (v/v)) and administered in the otherwise sterile drinking water (PBS). The mice in each respective group received $2.55 \times 10^8$ cfu/ml of UCC 118 and $2.35 \times 10^8$ cfu/ml of UCC 35624 daily for the duration of the feeding period. Control mice received sterile milk diluted in sterile phosphate buffered saline (PBS) and were maintained under identical conditions as the test group.

Experimental Design

All CB-17-mice were administered their respective feed according to their grouping for 2 days prior to injection with the $CD4^+$ $CD45RB^{high}$ cells. The sorted donor lymphocytes ($3–4 \times 10^5$) were represented in 200 μl of sterile PBS and injected i.p. into the recipient CB-17 SCID mice. All mice were weighed initially, then twice weekly thereafter. They were observed for clinical signs of illness: hunched over appearance, piloerection of the coat and diarrhoea.

Evaluation of the Effects of the Administered Probiotics on the Numbers of Indigenous Bacteria Culturable from Mouse Faeces.

The influence exerted by the administered UCC 118 and UCC 35624 when either administered alone or in combination with each other, on the microflora of the CB-17 SCID murine gut was investigated. Faecal samples were collected from each mouse weekly, weighed and resuspended in 10 ml PBS. The samples were then serially diluted in PBS and either pour plated or spread plated in appropriate dilutions on appropriate media in duplicate. The following bacterial groups were enumerated: *lactobacilli; bifidobacteria; enterococci*; bacteroides and coliforms. The selective media used were; de Mann Rogosa & Sharpe (S) agar; MRS agar supplemented with 0.2% lithium chloride (BDH), 0.3% sodium propionate (Fluke chemie), 0.5% cysteine hydrochloride (Sigma), and 5% sheep's blood; Slanetz and Bartley agar; Wilkins and Chalgren agar supplemented with anaerobic supplement SR 108 and 5% horse blood; and Violet Red Bile Agar. (All Oxoid unless otherwise stated). VRBA and Slanetz and Bartley plates were incubated aerobically for 24 and 45 h respectively. All other plates were incubated anaerobically for 48 h at 37° C.

Enumeration of Culturable Indigenous Flora from Specific Segments of the CB. 17 SCID Murine G.I.T.

After the feeding period all mice were sacrificed and dissected. Segments of the ileal-caecal region, small intestine, and the large intestine were removed. A peripheral lymph node (PLN), mesenteric lymph node (MLN) and a piece of the spleen were also taken. All tissues were weighed before being resuspended in 10 nil of PBS. Samples were then homogenised and serially diluted in PBS and either spread plated or pour plated in appropriate dilutions on appropriate media in duplicate. The bacterial groups were enumerated the same as those enumerated in the faecal analysis and samples were incubated as described previously.

Preparation of Intraepithelial and Lamiinapropria Lymphocytes

The isolation of the mucosal lymphocytes was carried out according to the method of Aranda, R. etal ((1997) supra).

Flow Cytometric Analysis of Lymphocyte Populations.

The analysis was conducted as described by Aranda, R et al. ((1997) supra)

Preparation of Tissue for Histopathological Analysis

Tissue samples were taken from the small intestine, large intestine, and ileal caecal region and fixed in 10% formalin. The procedure was as described in Aranda, R. et al. ((1997) supra).

Figure 3:
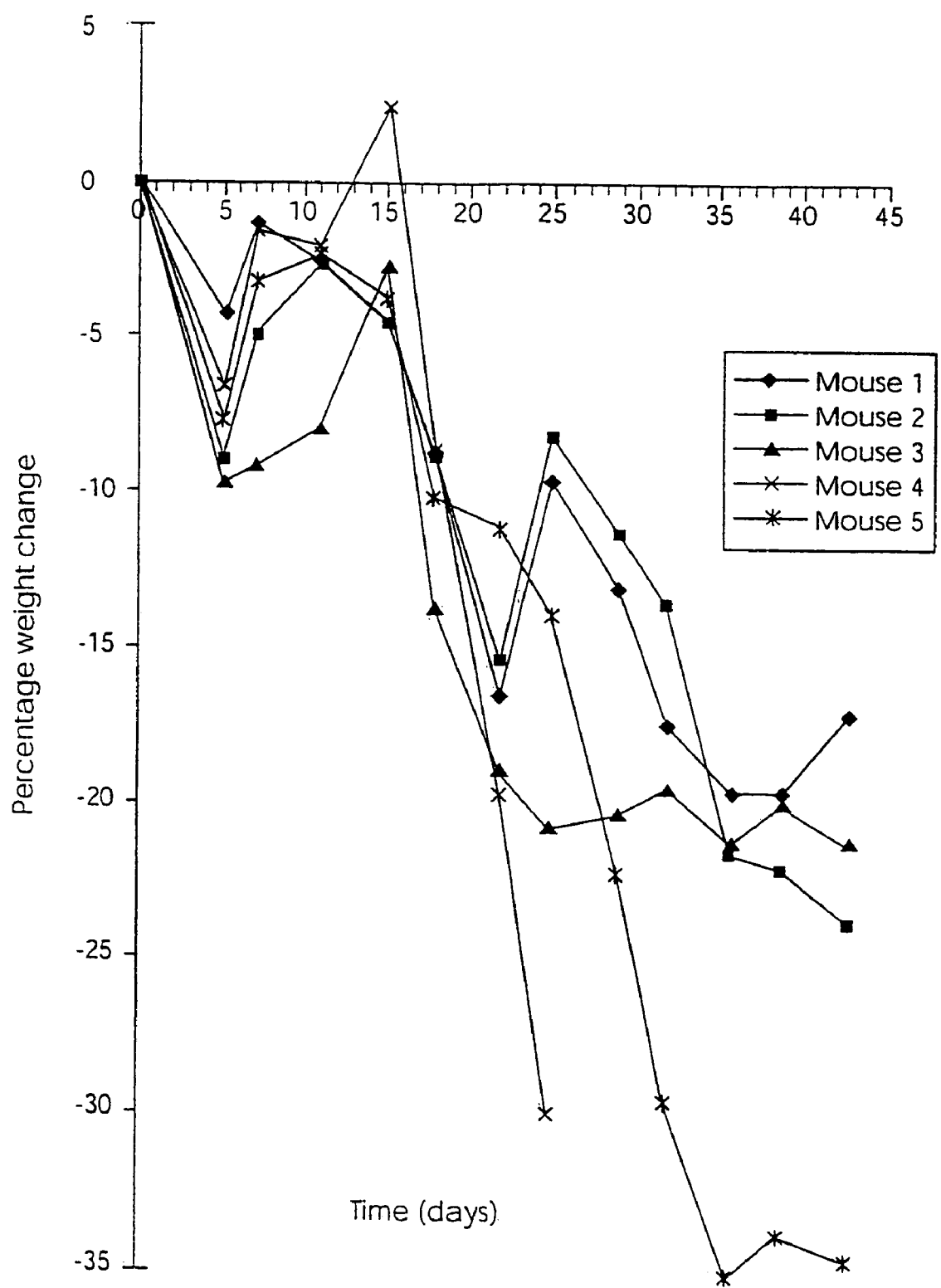
FIG. 3 is a graph of percentage weight change versus time (days) for five SCID mice (1–5) administered strain UCC 35624 as described in Example 5.
Figure 4:
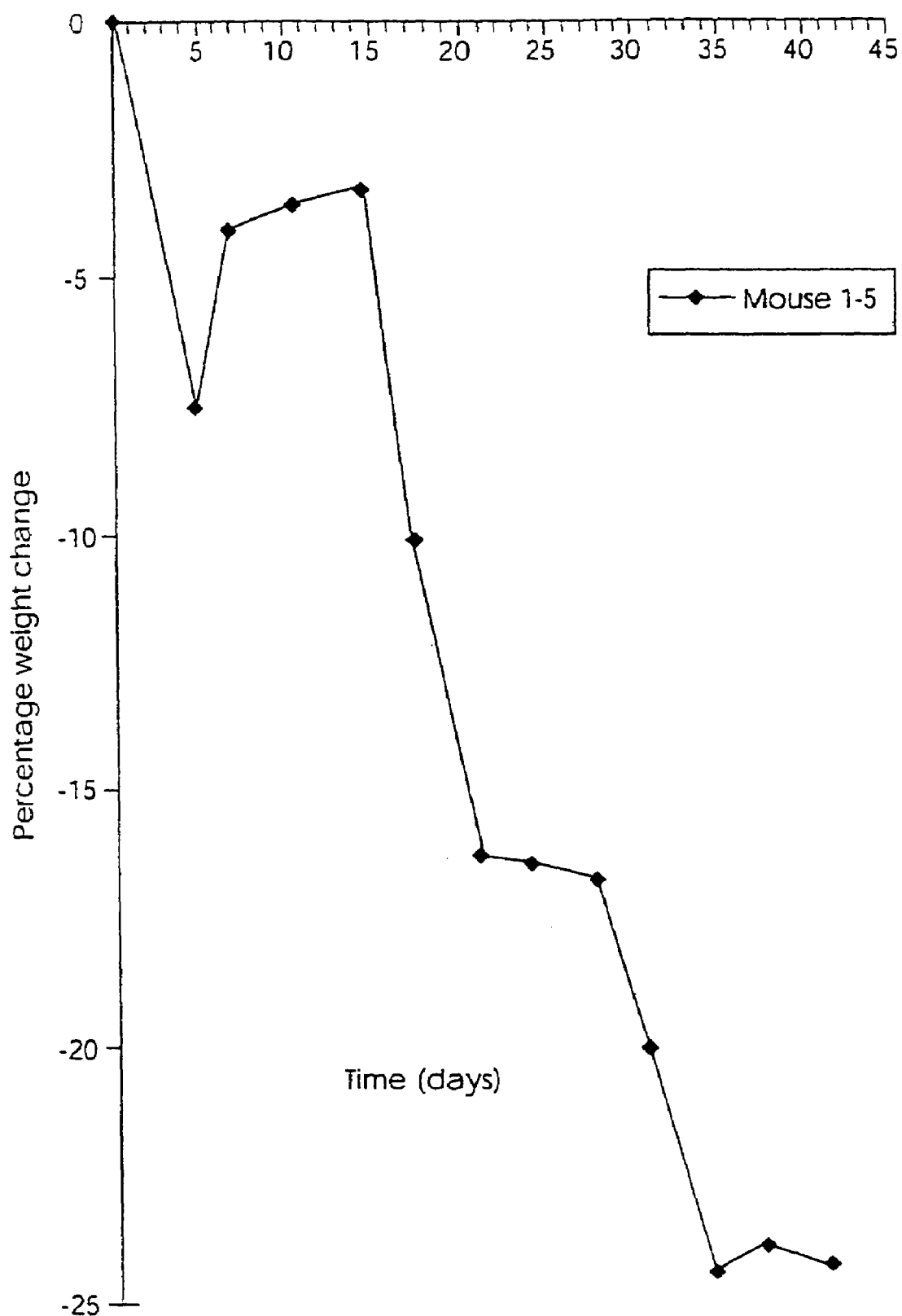
FIG. 4 is a graph of average percentage weight change versus time (days) for the SCID mice (1–5) administered strain UCC 35624 as described in Example 5.

It was observed from the experiment carried out that, consistent with previous results, the SCID mice reconstituted with $CD4^+$ $CD45RB^{high}$ T lymphocytes and consuming skim milk alone (control) developed a progressive wasting disease, identified by their significant weight loss. Disease became apparent at about 2 and a half to three weeks and the sick mice characteristically manifested a hunched over appearance, piloerection of their coat, and loose stool. One of the mice in the control group (mouse 4) died after 25 days and mice 1, 2, 3 and 5 showed a –20%, 25%, 21% and –35% percentage weight change respectively as depicted in FIGS. 3 and 4.

Figure 5:
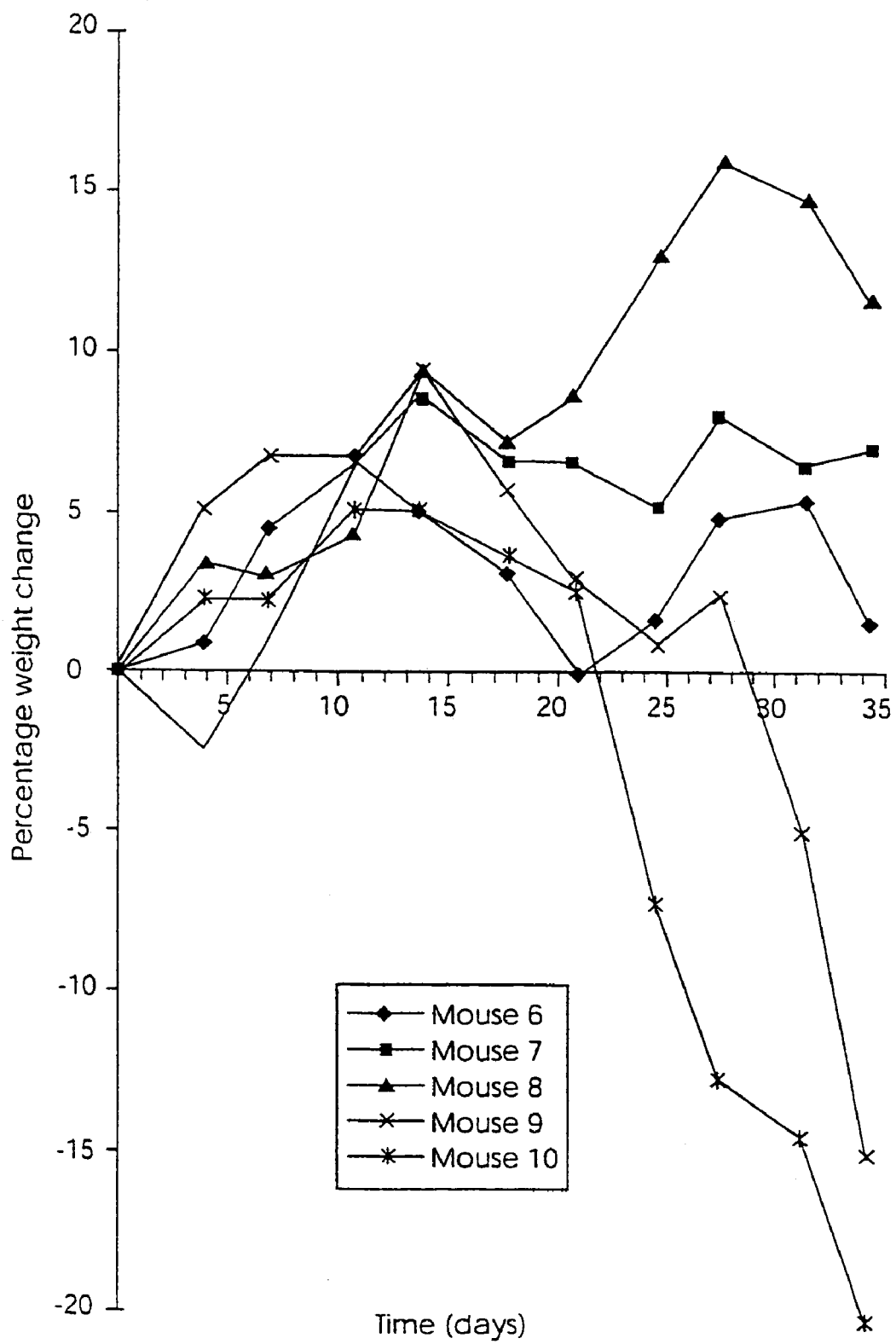
FIG. 5 is a graph of percentage weight change versus time (days) for mice (6–10) administered a combination of strains *Lactobacillus salivarius* UCC 118 and UCC 35624 as described in Example 5.
Figure 6:
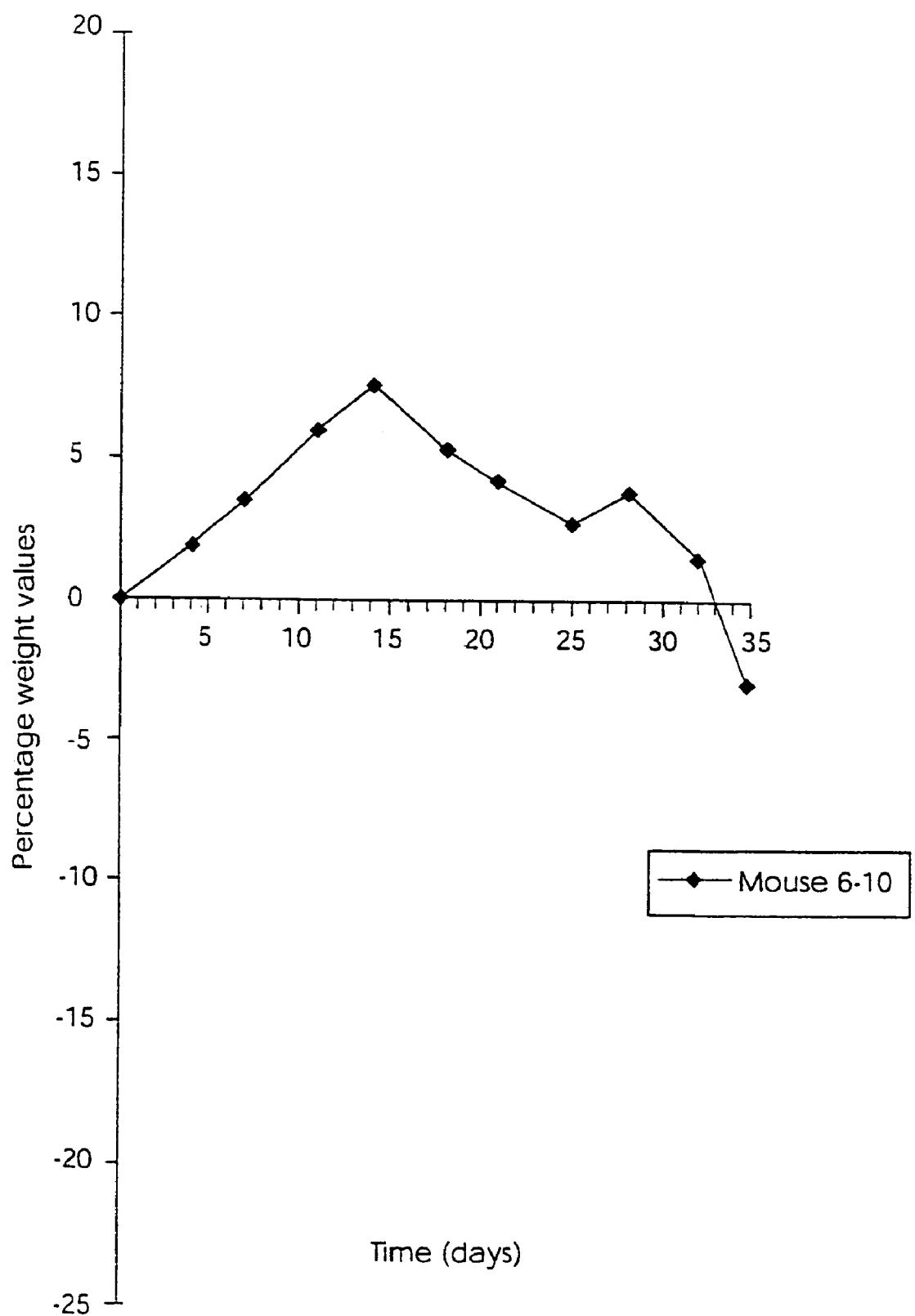
FIG. 6 is a graph of average percentage weight change versus time (days) for mice (6–10) administered a combination of strains UCC 118 and UCC 35624 as described in Example 5.

CB-17 SCID mice consuming UCC 118 alone gave a similar result as the controls with the characteristic weight loss. Mouse 3 died after 14 days, and mice 4, 5 and 6 showed a –15%, –25% and –28% percentage weight change respectively (data not shown). The mice consuming a combination of UCC 118 and UCC 35624 were found to have a marked improvement on the control mice. These mice did not lose as much weight as the control mice over the feeding period. Even after 35 days three of the mice in this group showed little percentage weight change. (FIGS. 5 and 6). Two of the mice in this group showed a weight loss only after about 30 days whereas control mice showed weight loss at 14 days (FIGS. 3 and 4).

Figure 7:
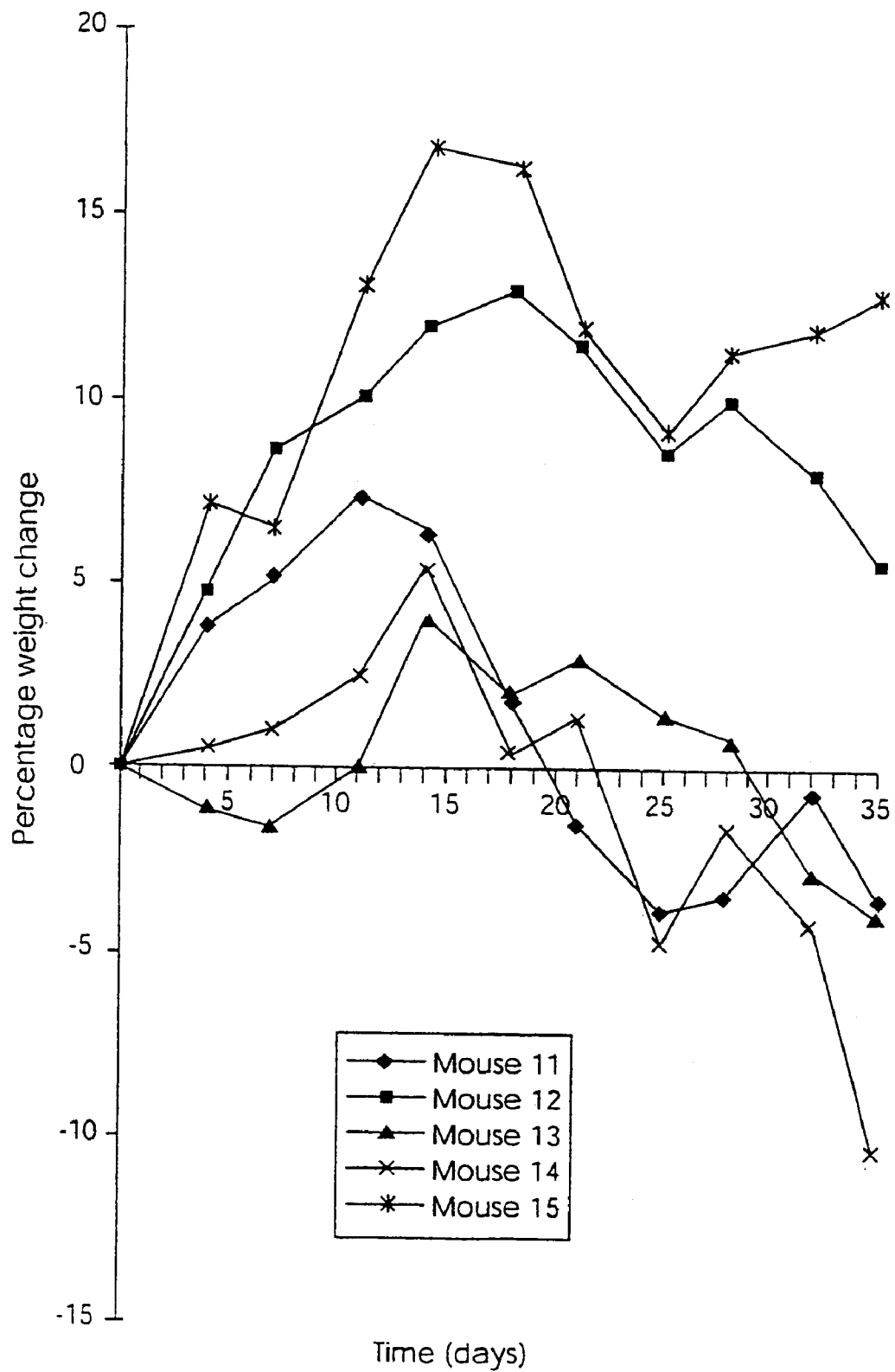
FIG. 7 is a graph of percentage weight change versus time (days) for mice (11–15) administered a combination of strains UCC 118 and UCC 35624 as described in Example 5.
Figure 8:
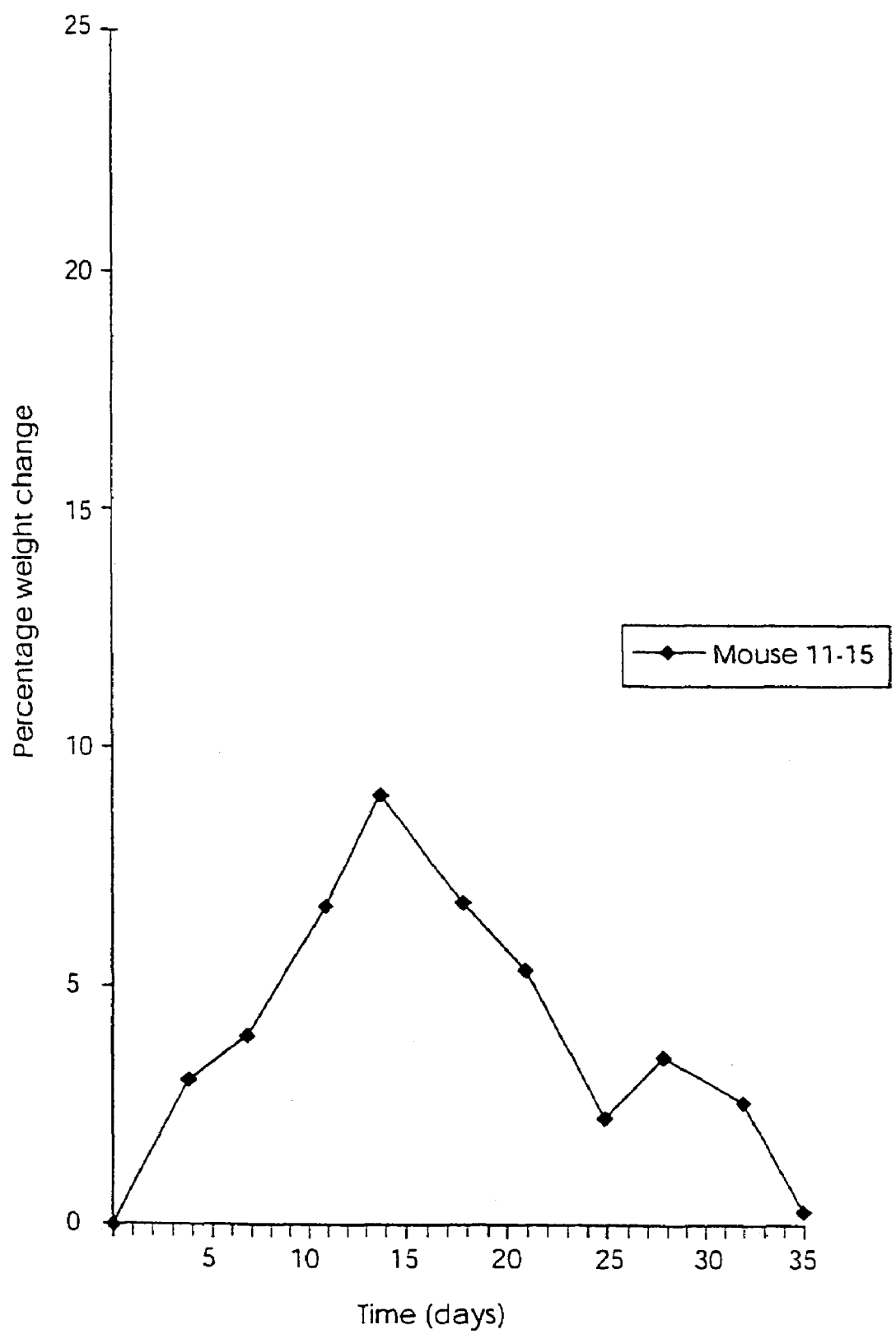
FIG. 8 is a graph of average percentage weight change versus time (days) for mice (11–15) administered a combination of strains UCC 118 and UCC 35624 as described in Example 5.

Mice consuming UCC 35624 alone appeared in good health and again weight loss when compared to the controls was considerably less (FIGS. 7 and 8). It can be concluded therefore that consumption of UCC 35624 either alone or in combination with UCC 118 alleviates the symptoms of inflammatory bowel disease.

Table 8 is a summary of experimental data for the study on the treatment of CD45RB colitis induced CB17 and SCID mice with a cocktail of UCC 118 and UCC 35624.

It was found in the studies that the mice were successfully reconstituted with lymphocytes and lymphocytes having been derived from the donor model (data not shown).

TABLE 8

Treatment of CD45RB colitis induced CB 17 SCID mice with a cocktail of *Lactobacillus salivarius* UCC 118 and *Bifidobacteria*.

| Organ | Mouse 1 Untreated (RB hi cells + skimmed milk) | Mouse 2 Untreated (RB hi cells + skimmed milk) | Mouse 3 Cocktail Treated | Mouse 4 Cocktail Treated | Mouse 5 Cocktail Treated | Mouse 6 Cocktail Treated |
|---|---|---|---|---|---|---|
| % weight loss | 31.25 | 27.74 | 14.50 | 14.05 | 21.88 | 11.18 |
| Final Appearance | looks ill | very ill | very healthy | slightly ill | healthy | healthy |
| Stool Appearance | very mushy | very mushy | mushy | solid | semi solid | semi solid |
| Colon Appearance | thickened | very thickened | slightly thickened | slight proximal thickening | slightly thickened | slight proximal thickening |
| No. SIEL | 100,000 | 200,000 | 0 | 0 | 512,000 | 28,000 |
| No. LIEL | 25,000 | 72,000 | 100,000 | 50,000 | 384,000 | 96,000 |
| No. SLPL | 200,000 | 100,000 | 264,000 | 200,000 | 640,000 | 104,000 |

TABLE 8-continued

Treatment of CD45RB colitis induced CB 17 SCID mice with a cocktail of *Lactobacillus salivarius* UCC 118 and *Bifidobacteria*.

| Organ | Mouse 1 Untreated (RB hi cells + skimmed milk) | Mouse 2 Untreated (RB hi cells + skimmed milk) | Mouse 3 Cocktail Treated | Mouse 4 Cocktail Treated | Mouse 5 Cocktail Treated | Mouse 6 Cocktail Treated |
|---|---|---|---|---|---|---|
| No. LLPL | 96,000 | 256,000 | 160,000 | 160,000 | 256,000 | 160,000 |
| No. MLN | 0 | N/A | 81,900 | N/A | 28,800 | N/A |
| No. PLN | 0 | 192,000 | 0 | 120,000 | 64,000 | 0 |
| Spleen # Lymphos. | 960,000 | 512,000 | 640,000 | 640,000 | 512,000 | 6,400,000 |
| CD3+/H-2Kb+ Flow correction % | | | | | | |
| No. SIEL | 62,000 | 114,000 | 0 | 0 | 450,560 | 17,920 |
| No. LIEL | 21,250 | 48,960 | 74,800 | 38,000 | 345,600 | 65,280 |
| No. SLPL | 74,000 | 42,000 | 158,400 | 136,000 | 384,000 | 66,460 |
| No. LLPL | 67,200 | 161,280 | 115,200 | 108,000 | 184,320 | 108,800 |
| No. MLN | 0 | N/A | 130,00 | N/A | 64,000 | N/A |
| No. PLN | 0 | 126,720 | 0 | 87,600 | 54,400 | 0 |
| Spleen | 518,400 | 102,400 | 211,200 | 307,200 | 230,400 | 4,480,000 |
| UCC 118 bacterial counts (per biopsy) post mortem | | | | | | |
| SI | 0 | 0 | 1,200 | 0 | 0 | 0 |
| LI | 0 | 0 | >30,000 | >30,000 | 100 | 11,600 |
| Caecum | 0 | 0 | >30,000 | >30,000 | >30,000 | >30,000 |
| Spleen | 0 | 0 | 0 | 1,350 | 0 | 0 |
| Colon Pathological Scoring | | | | | | |
| A (0–3) | — | 1.0 | 1.0 | 2.0 | — | — |
| B (0–2) | — | 1.5 | 1.0 | 1.0 | — | — |
| C (0–3) | — | 2.5 | 1.0 | 2.0 | — | — |
| D (0–3) | — | 2.0 | 3.0 | 3.0 | — | — |
| E (1–3) | — | 1.0 | 1.0 | 2.0 | — | — |
| Remarks | | | | | | |
| Total Score | — | 8.0 | 7.0 | 10.0 | — | — |

A: Degree of inflammatory infiltrate;
B: Mucin depletion;
C: Epithelia hyperplasia;
D: No. of TEL in the crypts;
E: No. of inflammatory foci per high power fields

EXAMPLE 7

In Vitro Studies to Examine the Immune Perception of *Bifidobacterium longum infantis*.

Figure 9:
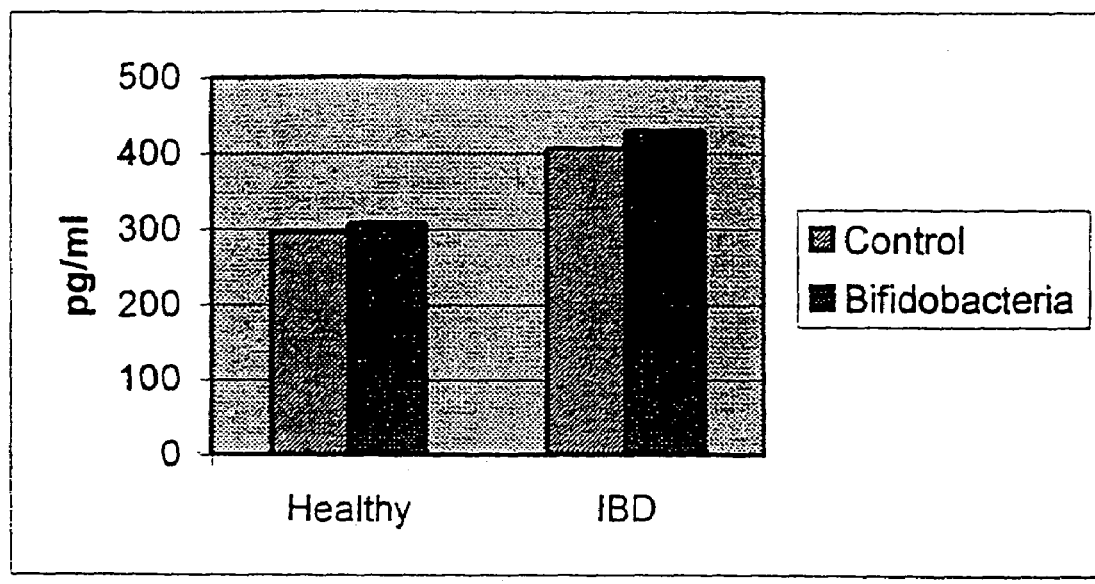
FIG. 9 is a bar chart of TNFα levels in patient and control samples in the presence of PBMCs and *Bifidobacteria longum infantis* as described in Example 7.

Overnight washed cultures of *Bifidobacteria* were incubated with human peripheral blood mononuclear cells (PBMCs) from both healthy volunteers (n=9) and patients suffering from inflammatory bowel disease (n=5). Production of the proinflammatory cytokine tumour necrosis factor α (TNFα) was measured by ELISA in seventy two hour culture supernatants. Co-incubation of *Bifidobacterium longum infantis* with human PBMCs did not result in the stimulation of TNFα production (FIG. 9). Thus, exposure of the systemic immune system to this bacterium does induce an inflammatory response.

Figure 10:
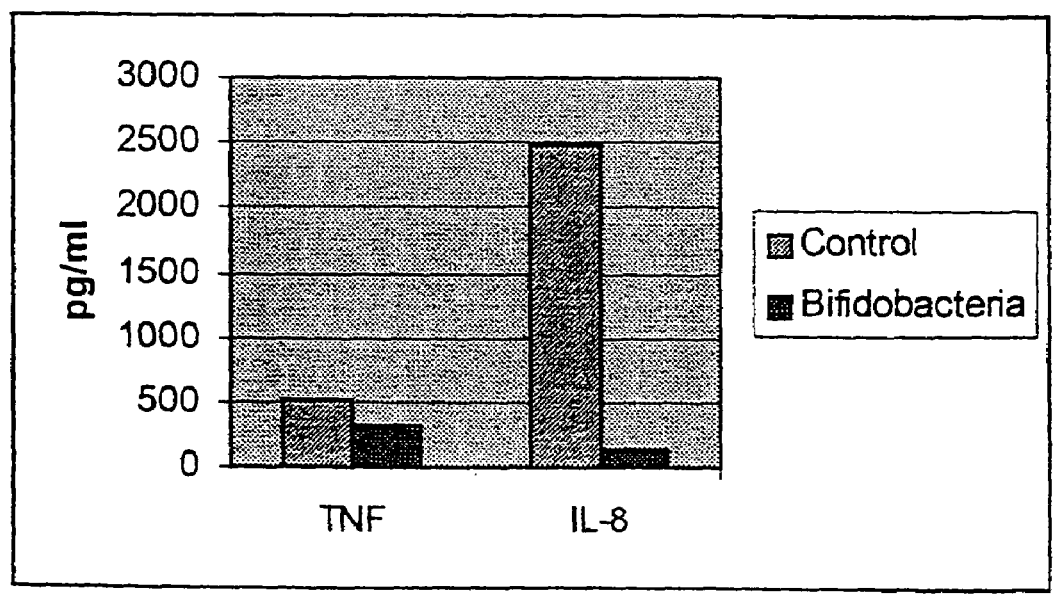
FIG. 10 is a bar chart showing TNFα and IL-8 levels in co-cultures of epithelial cells, PBMCs and *Bifidobacterium longum infantis* as described in Example 7. Controls represent co-cultures of epithelial cells and PBMCs alone.

In order to assess the immune perception of *Bifidobacterium longum infantis* at mucosal surfaces, co-culturing of epithelial cells and PBMCs was performed in transwell chambers. Briefly, an epithelial cell monolayer was grown in the upper chamber and PBMCs were incubated in the lower compartment. These were seperated from each other by a porous membrane which allowed the passage of soluble mediators between the two compartments but did not allow cell-cell contact. Using this model, the production of TNFα and Interleukin-8 (IL-8) was measured in the presence and absence of *Bifidobactertium longum infantis* in the PBMC compartment. Co-culture of epithelial cells, PBMCs and *Bifidobacterium longum infantis* resulted in significant suppression of TNFα and IL-8 production (FIG. 10). Thus, a tri-cellular network involving epithelial cells, PBMCs and *Bifidobacterium longum infantis* results in suppression of proinflammatory cytokine production.

EXAMPLE 8

In Vivo Anti-Inflammatory activity of *Bifidobacterium longum infantis*

*Bifidobacterium longum infantis* ($1 \times 10^9$ cells per day) was consumed by 18 healthy humans in a fermented milk (yoghurt) product for three weeks. Serum was collected for cytokine analysis pre and post consumption of this probiotic strain. Faecal samples were obtained for microbiological analysis.

Figure 11:
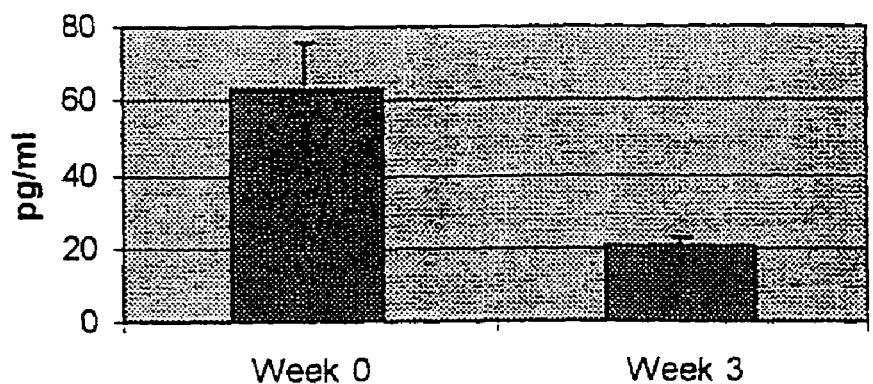
FIG. 11 are bar charts of peripheral blood cytokine levels following consumption of *Bifidobacerium longum infantis* by healthy human volunteers (n=18) for three weeks as described in Example 8.
Figure 11:
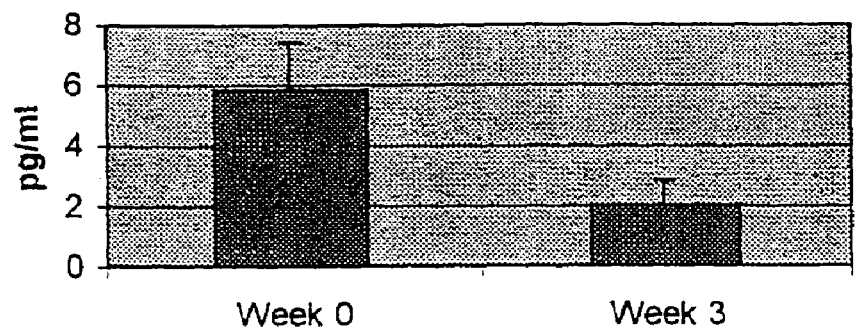
Figure 11:
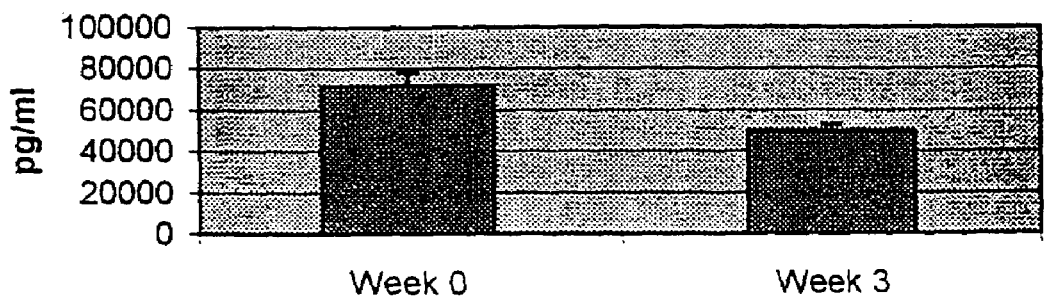
Figure 12:
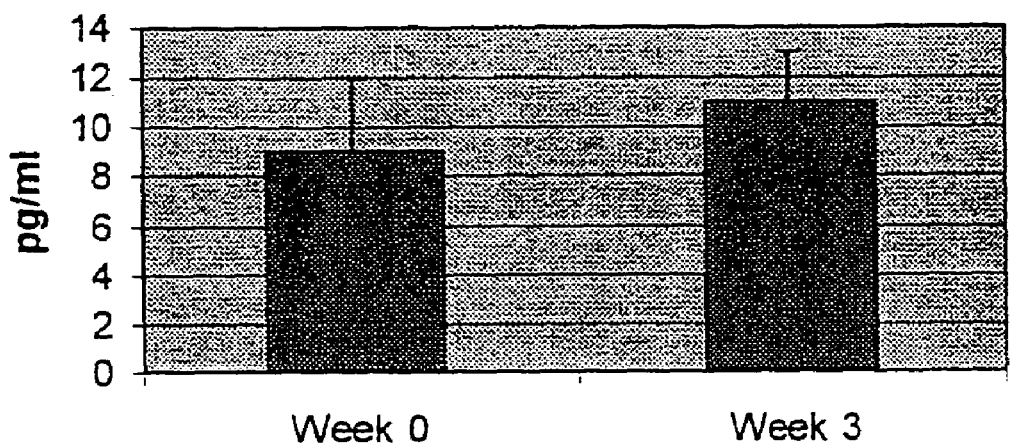
FIG. 12 are bar charts of serum levels of TNFα and IL-LRA following consumption of *Bifidobacterium longum infantis* to healthy human volunteers (n=18) as described in Example 8.
Figure 12:
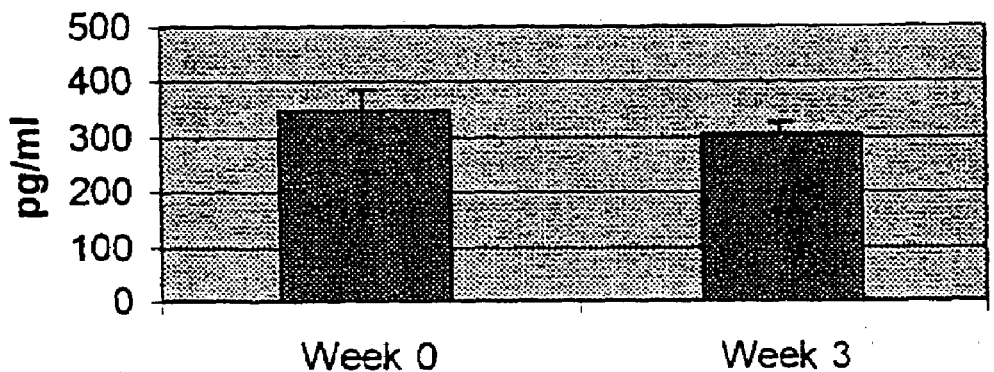

Considerable modification of peripheral blood cytokine levels were observed in this feeding study. Serum soluble Interleukin-6 receptor (sIL-6R, p=0.007), Interferon-γ (IFNγ, p=0.041) and IL-8 (p=0.004) levels were significantly reduced following consumption of this probiotic strain (FIG. 11). No alteration in serum TNFα and Interleukin-1 receptor antagonist (IL-1RA) levels were observed (FIG. 12). *Bifidobacterium longum infantis* was detected at approximately 1×10⁵ colony forming units per gram of faecal matter over the course of this feeding study.

Targeted in vitro selection criteria reflecting the complex interactions of the GI environment allow for the identification of probiotic strains capable of functioning effectively when reintroduced into that environment. Using the selection criteria outlined above, the probiotic bacteria *Bifidobacterium longum infantis* has demonstrable immunomodulating properties in vitro. Following consumption by SCID mice and human volunteers, significant modification of systemic immune parameters was noted. Thus, the use of *Bifidobacterium longum infantis* as a biotherapeutic agent in the treatment of immune mediated diseases is warranted.

EXAMPLE 9

Figure 13:
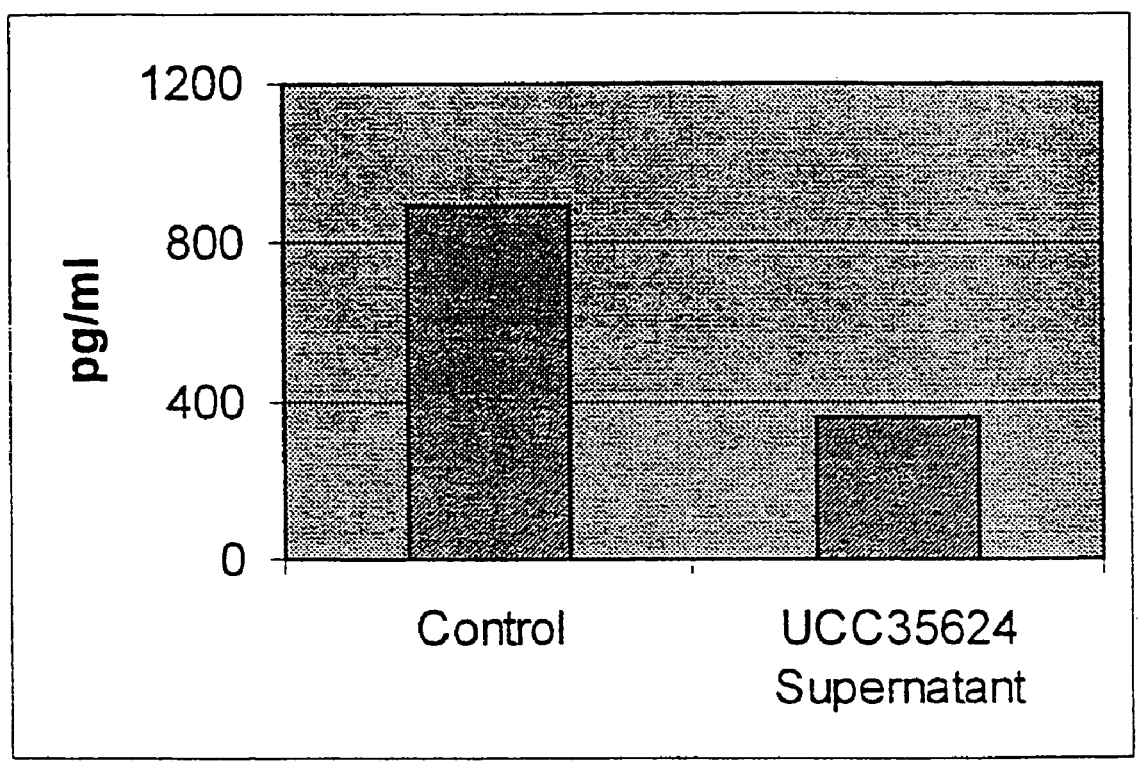
FIG. 13 is a bar chart of TNFα levels in cell-free spent culture supernatant of *Bifidobacterium longum infantis* and an MRS control as described in Example 9.

Measurement of TNFα in *Bifidobacterium longum infantis* UCC 35624 Cell Free Supernatant Overnight cultures of *Bifidobacterium longum infantis* were centrifuged and the cell-free culture supernatant was examined for the presence of cytokine inhibitors. Cell free supernatants were incubated with human TNFα for 20 minutes at 37° C. TNFα levels were quantified thereafter by ELISA. Following exposure to the *Bifidobacteria* supernatant, TNFα levels were significantly reduced (FIG. 13). Thus, *Bifidobactenum longum infantis* UCC35624 secretes a factor that antagonises TNFα activity. Production of this factor by *Bifidobacterium longum infantis* at the surface of the gastrointestinal tract, in vivo, would significantly restrict the host inflammatory response.

This indicates that the antagonism of TNFα also occurs at a molecular level due to a soluble factor released by UCC 35624.

Inflammation

Inflammation is the term used to describe the local accumulation of fluid, plasma proteins and white blood cells at a site that has sustained physical damage, infection or where there is an ongoing immune response. Control of the inflammatory response is exerted on a number of levels (for review see Henderson B., and Wilson M. 1998. In "Bacteria-Cytokine interactions in health and disease. Portland Press, 79–130). The controlling factors include cytolines, hormones (e.g. hydrocortisone), prostaglandins, reactive intermediates and leukotrienes. Cytokines are low molecular weight biologically active proteins that are involved in the generation and control of immunological and inflammatory responses, while also regulating development, tissue repair and haematopoiesis. They provide a means of communication between leukocytes themselves and also with other cell types. Most cytokines are pleiotrophic and express multiple biologically overlapping activities. Cytokine cascades and networks control the inflammatory response rather than the action of a particular cytokine on a particular cell type (Arai K I, et al., Annu Rev Biochem 1990; 59:783–836). Waning of the inflammatory response results in lower concentrations of the appropriate activating signals and other inflammatory mediators leading to the cessation of the inflammatory response. TNFα is a pivotal proinflammatory cytokine as it initiates a cascade of cytokines and biological effects resulting in the inflammatory state. Therefore, agents which inhibit TNFα are currently being used for the treatment of inflammatory diseases, e.g. infliximab.

Pro-inflammatory cytokines are thought to play a major role in the pathogenesis of many inflammatory diseases, including inflammatory bowel disease (IBD). Current therapies for treating IBD are aimed at reducing the levels of these pro-inflammatory cytokines, including IL-8 and TNFα. It has been suggested that such therapies may also play a significant role in the treatment of systemic inflammatory diseases such as rheumatoid arthritis. Humans fed with yoghurt containing *Bifidobacterium longum infantis* UCC35624 have shown marked decreases in their systemic levels of IL-8. This strain may therefore have potential application in the treatment of a range of inflammatory diseases, particularly if used in combination with current anti-inflammatory therapies, such as non-steroid anti-inflammatory drugs (NSAIDs) or Infliximab.

Diarrhoeal Disease.

The barrier function of the intestinal epithelium can be diminished during nervous (acetylcholine) and immune (histamine) mediated secretion. Certain bacterial toxins may also induce $Ca^{2+}$ and PKC dependent secretion and thereby can disturb the epithelial barrier (Ganguly N K and Kaur T. Indian J Med Res 1996; 104:28–37, Groot J A. Vet Q 1998; 20(S3):45–9). Several studies have examined the prevention and treatment of diarrhoea using probiotic bacteria. Prospective studies have demonstrated the efficacy of lactic acid bacteria administration for both prophylactic and therapeutic use against diarrhoea in pre-mature infants, new borns, children (Isolauri E, et al., Dig Dis Sci 1994 December; 39(12):2595–600) and in the treatment of antibiotic related diarrhoea (Siitonen S, et al., Ann Med 1990 February; 22(1):57–9) and traveller's diarrhoea (Oksanen P J, et al., Ann Med 1990 February; 22(1):53–6).

Figure 14:
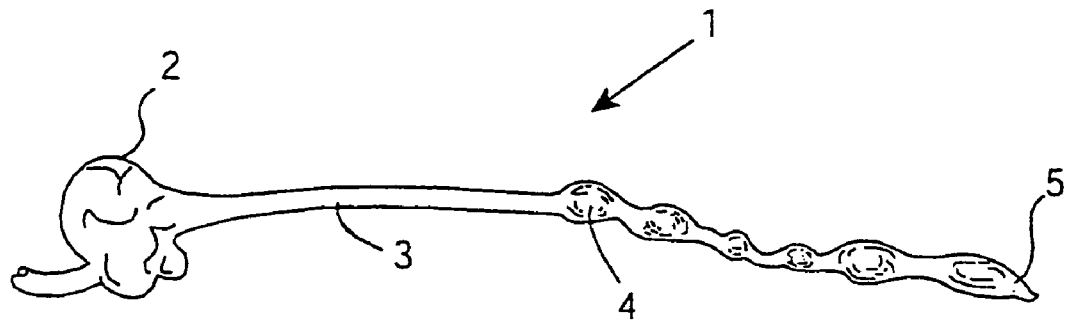
FIG. 14 is a diagrammatic representation of a SCID mouse lower intestine after treatment with *Bifidobacterium longum infantis*.
Figure 15:
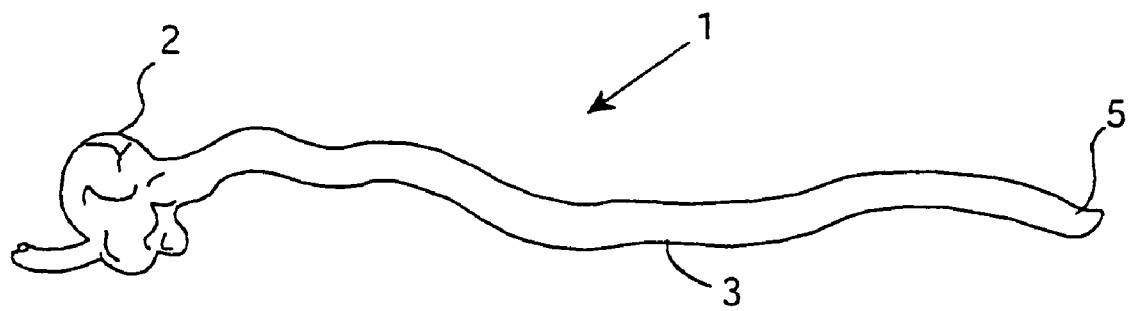
FIG. 15 is a diagrammatic representation of the lower intestine of an untreated SCID mouse.

We have examined consumption of *Bifidobacterium longum infantis* UCC 35624 by SCID mice. It was found that inflammatory activity was significantly attenuated and mice consuming *Bifidobacterium longum infantis* UCC 35624 retained solid stools while control mice suffered from diarrhoea. FIGS. 14 and 15 illustrate the lower intestine of treated and untreated SCID mice. The lower intestine shown includes the caecum 2, intestine 3 and anus 5. In FIG. 14 the mice were treated with *Bifidobacterium longum infantis* UCC 35624 and it is apparent that solid stools 4 have been retained in the intestine. In comparison FIG. 15 shows the untreated mouse intestine 3, characteristically inflamed. No water absorption has occurred so that no solid stools are retained resulting in diarrhoea.

The anti-diarrhoeal effect observed may be related to the anti-inflammatory activity, possibly mediated via cAMP modulation. Cyclic AMP-dependent Cl-secretion is the major secretory pathway in the human intestine (Brzuszczak I M, et al., J. Gastroenterol. Hepatol. 1996; 11(9):804–10). It can be inferred that the anti-diarrhoeal effect of *Bifidobacterium longum infantis* UCC 35624 is not restricted just to diarrhoea resulting from gastrointestinal inflammation, but can be applied to the general treatment of diarrhoeal disease.

Autoimmune Disease

The immune system has a large repertoire of specificities expressed by B and T cells. Some of these specificities will be directed to self-components. Self-recognition is normally controlled by clonal deletion and inactivation of self-reactive lymphocytes. However, there is a constant background of autoimmunity with antibodies to many proteins being found in serum. A breakdown in the self-nonself recognition system results in autoimmunity. When autoimmune disease does occur, the resulting immune response damages the tissue bearing the offending antigen. Immune complex deposition, type II hypersensitivity and cell-mediated reactions are the most important mechanisms by which immunopathological damage occurs. Examples of autoimmune diseases include, but are not limited to, systemic lupus erythematosus, rheumatoid arthritis, insulin dependent diabetes mellitus, myasthenia gravis and pernicious anaemia. *Bifidobacterium longum infantis* and *Lactobacillus salivarius* subsp. *salivarius* are immunomodulatory bacteria. Thus, consumption either as single components or in combination of these bacteria by patients suffering from autoimmune disease may restrict organ damage and help restore normal body homeostasis.

Inflammation and Cancer

The production of multifunctional cytokines across a wide spectrum of tumour types suggests that significant inflammatory responses are ongoing in patients with cancer. It is currently unclear what protective effect this response has against the growth and development of tumour cells in vivo. However, these inflammatory responses could adversely affect the tumour bearing host. Complex cytokine interactions are involved in the regulation of cytokine production and cell proliferation within tumour and normal tissues (McGee D W, et al., Immunology 1995 September; 86(1): 6–11, Wu S, et al., Gynecol Oncol 1994 April; 53(1):59–63). It has long been recognised that weight loss (cachexia) is the single most common cause of death in patients with cancer (Inagaki J, et al., Cancer 1974 February; 33(2):568–73) and initial malnutrition indicates a poor prognosis (Van Eys J. Nutr Rev 1982 December; 40(12):353–9). For a tumour to grow and spread it must induce the formation of new blood vessels and degrade the extracellular matrix. The inflammatory response may have significant roles to play in the above mechanisms, thus contributing to the decline of the host and progression of the tumour. Due to the anti-inflammatory nature of these bacterial strains, they may reduce the rate of malignant cell transformation. Furthermore, intestinal bacteria can produce, from dietary compounds, substances with genotoxic, carcinogenic and tumour-promoting activity and gut bacteria can activate pro-carcinogens to DNA reactive agents (Rowland I. R. (1995). Toxicology of the colon: role of the intestinal microflora. In: Gibson G. R. (ed). Human colonic bacteria: role in nutrition, physiology and pathology, pp 155–174. Boca Raton CRC Press). In general, species of *Bifidobacteria* and *Lactobacillus* have low activities of xenobiotic metabolising enzymes compared to other populations within the gut such as bacteroides, eubacteria and clostridia (Saito Y., et al., Microb. Ecol. Health Dis., 1992; 5, 105–110). Therefore, increasing the number of lactic acid bacteria in the gut could beneficially modify the levels of these enzymes.

Prebiotics

The introduction of probiotic organisms is accomplished by the ingestion of the microorganism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract (Gibson, G R. Br. J. Nutr. 1998; 80 (4):S209–12). Prebiotics refers to any non-viable food component that is specifically fermented in the colon by indigenous bacteria thought to be of positive value, e.g. *bifidobacteria, lactobacilli*. Types of prebiotics may include those which contain fructose, xylose, soya, galactose, glucose and mannose. The combined administration of a probiotic strain with one or more prebiotic compounds may enhance the growth of the administered probiotic in vivo resulting in a more pronounced health benefit, and is termed synbiotic.

Other Active Ingredients

It will be appreciated that the *Bifidobacterium* may be administered prophylactically or as a method of treatment either on its own or with other probiotic and/or prebiotic materials as described above. In addition, the bacteria may be used as part of a prophylactic or treatment regime using other active materials such as those used for treating inflammation or other disorders, especially those of the gastrointestinal tract. Such combinations may be administered in a single formulation or as separate formulations administered at the same or different times and using the same or different routes of administration.

The invention is not limited to the embodiments hereinbefore described which may be varied in detail.

The invention claimed is:

1. An isolated strain of *Bifidobacterium* NCIMB 41003.
2. The strain of claim 1 in the form of viable cells.
3. The strain of claim 1 in the form of non-viable cells.
4. A formulation comprising the strain of claim 1.
5. The formulation of claim 4 further comprising at least one further strain of *Bifidobacterium*.
6. The formulation of claim 4, further comprising a probiotic material.
7. The formulation of claim 4, further comprising a prebiotic material.
8. The formulation of claim 4, further comprising a strain of *Lactobacillus salivarius*.
9. The formulation of claim 8, wherein the strain of *Lactobacillus salivarius* is in the form of viable cells.
10. The formulation of claim 8, wherein the strain of *Lactobacillus salivarius* is in the form of non-viable cells.
11. The formulation of claim 8, wherein the strain of *Lactobacillus salivarius* is isolated from a resected and washed human gastrointestinal tract and is significantly immunomodulatory following oral consumption in humans.
12. The formulation of claim 11, wherein the strain of *Lactobacillus salivarius* inhibits the growth of Gram positive bacteria, Gram negative bacteria, or both.
13. The formulation of claim 12, wherein the strain of *Lactobacillus salivarius* secretes a product having antimicrobial activity into a cell-free supernatant that is produced only by growing cells and is destroyed by proteinase K and pronase E, wherein the inhibition of growth and antimicrobial activity are maintained in the presence of physiological concentrations of human bile and human gastric juice.
14. The formulation of claim 8, wherein the strain of *Lactobacillus salivarius* is *Lactobacillus salivarius* strain NCIMB 40829 or a mutant or a variant thereof.
15. The formulation of claim 14, wherein the mutant is a genetically modified mutant.
16. The formulation of claim 14, wherein the variant is a naturally occurring variant.
17. The formulation of claim 4, further comprising an ingestible carrier.
18. The formulation of claim 17, wherein the ingestible carrier is a pharmaceutically acceptable carrier.
19. The formulation of claim 18, wherein the pharmaceutically acceptable carrier is in the form of a capsule, a tablet, or a powder.
20. The formulation of claim 17, wherein the ingestible carrier is a food product.
21. The formulation of claim 20, wherein the food product is acidified milk, a yogurt, a frozen yogurt, a milk powder, a milk concentrate, a cheese spread, a dressing, or a beverage.

22. The formulation of claim 4, further comprising a protein, a peptide, a lipid, a carbohydrate, a vitamin, a mineral, or a trace element.

23. The formulation of claim 22, wherein the protein or the peptide is rich in glutamine, glutamate, or both.

24. The formulation of claim 4, wherein the *Bifidobacterium* is present at more than $10^6$ cfu per gram of the formulation.

25. The formulation of claim 4, further comprising an adjuvant.

26. The formulation of claim 4, further comprising a bacterial component.

27. The formulation of claim 4, further comprising a drug entity.

28. The formulation of claim 4, further comprising a biological compound.

29. The formulation of claim 4, wherein the formulation is suitable for oral administration to a subject.

30. A foodstuff comprising the strain of *Bifidobacterium* of claim 1.

31. A foodstuff comprising the formulation of claim 4.

32. A pharmaceutical composition comprising the *Bifidobacterium* strain of claim 1 and a pharmaceutically acceptable carrier.

33. A pharmaceutical composition comprising the formulation of claim 4 and a pharmaceutically acceptable carrier.

* * * * *